US008617059B2

(12) United States Patent
Kanzaki

(10) Patent No.: US 8,617,059 B2
(45) Date of Patent: Dec. 31, 2013

(54) ENDOSCOPIC APPARATUS AND ENDOSCOPE ADAPTER

(75) Inventor: Kazuhiro Kanzaki, Tokyo (JP)

(73) Assignee: Olympus Corporation, Tokyo (JP)

( * ) Notice: Subject to any disclaimer, the term of this patent is extended or adjusted under 35 U.S.C. 154(b) by 1207 days.

(21) Appl. No.: 11/601,920

(22) Filed: Nov. 20, 2006

(65) Prior Publication Data

US 2007/0203397 A1 Aug. 30, 2007

(30) Foreign Application Priority Data

May 27, 2005 (JP) ................ P2005-155845
May 31, 2005 (JP) ................ P2005-160297

(51) Int. Cl.
*A61B 1/06* (2006.01)

(52) U.S. Cl.
USPC ................... 600/175; 600/172; 600/160

(58) Field of Classification Search
USPC ............ 600/127, 129, 160, 172, 175, 179
See application file for complete search history.

(56) References Cited

U.S. PATENT DOCUMENTS

| | | | | |
|---|---|---|---|---|
| 4,534,339 | A | * | 8/1985 | Collins et al. ............. 600/136 |
| 4,926,757 | A | * | 5/1990 | Spencer .................. 105/224.1 |
| 4,974,075 | A | * | 11/1990 | Nakajima ................... 348/75 |
| 4,998,182 | A | * | 3/1991 | Krauter et al. ............. 361/730 |
| 5,287,191 | A | * | 2/1994 | Suzuki et al. ............. 348/375 |
| 5,518,501 | A | * | 5/1996 | Oneda et al. ............. 600/127 |
| 5,609,561 | A | * | 3/1997 | Uehara et al. ............. 600/112 |
| 5,634,466 | A | * | 6/1997 | Gruner .................... 600/459 |
| 5,662,588 | A | * | 9/1997 | Iida ........................ 600/121 |

(Continued)

FOREIGN PATENT DOCUMENTS

| | | |
|---|---|---|
| JP | 02-160211 | 6/1990 |
| JP | H10-328131 | 12/1998 |

(Continued)

OTHER PUBLICATIONS

Japanese Office Action of corresponding Application No. JP 2005-160297 dated Mar. 15, 2011.

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

An endoscope adapter for use with an endoscope is provided. The endoscope includes an endoscopic insertion section subject to be inserted into an object subject to inspection and the endoscope adapter so that the endoscopic insertion section has an insertion section electrodes; the endoscope adapter comprises a lighting section for emitting light to the object and an adapter electrode section connected to the lighting section. The adapter electrode section comprises: an elongated hollow casing having an opening section at one end in the longitudinal direction of the casing; and a columnar electrode terminal configured to be movable in the longitudinal direction in the hollow casing and capable of projecting from the longitudinal direction end of the hollow casing. The inner diameter of the opening section is equalized to the outer diameter of the electrode terminal. It is possible to provide an endoscopic apparatus and an endoscope adapter having an endoscope adapter and an endoscopic insertion section not so significant in sizes; being capable of closing an opening section in a state where the endoscope adapter is attached to the endoscopic insertion section; and being capable of maintaining the electrode terminal clean for a prolonged period.

7 Claims, 38 Drawing Sheets

(56) References Cited

U.S. PATENT DOCUMENTS

| | | | |
|---|---|---|---|
| 5,682,199 A * | 10/1997 | Lankford | 348/72 |
| 6,036,636 A | 3/2000 | Motoki et al. | |
| 6,095,970 A * | 8/2000 | Hidaka et al. | 600/110 |
| 7,691,056 B2 * | 4/2010 | Hirata | 600/129 |
| 2001/0056280 A1 * | 12/2001 | Underwood et al. | 606/41 |
| 2004/0143162 A1 * | 7/2004 | Krattiger et al. | 600/175 |
| 2004/0171914 A1 * | 9/2004 | Avni | 600/160 |
| 2005/0177027 A1 | 8/2005 | Hirata | |
| 2005/0182291 A1 * | 8/2005 | Hirata | 600/101 |
| 2006/0058584 A1 * | 3/2006 | Hirata | 600/179 |
| 2006/0069309 A1 * | 3/2006 | Ono | 600/134 |
| 2007/0191684 A1 * | 8/2007 | Hirata | 600/179 |

FOREIGN PATENT DOCUMENTS

| | | |
|---|---|---|
| JP | 2004-341546 | 12/2004 |
| JP | 2004-341547 | 12/2004 |
| JP | 2005-110879 | 4/2005 |
| JP | 2005-118137 | 5/2005 |
| JP | 2005-218781 | 8/2005 |

OTHER PUBLICATIONS

Japanese Office Action of corresponding Application No. JP 2005-155845 dated Mar. 15, 2011.

* cited by examiner

ENDOSCOPIC APPARATUS AND ENDOSCOPE ADAPTER

BACKGROUND OF THE INVENTION

1. Field of the Invention

The present invention relates to an endoscopic apparatus for observing an object subject to inspection and an endoscope adapter.

2. Description of the Related Art

A variously operable endoscopic apparatus for use in various fields, e.g., medical field or industrial field is provided with an elongated endoscopic insertion section subject to be inserted into an object subject to inspection; and an endoscope main body section. An endoscope adapter provided with a lighting section, etc., is detachably attached at the tip of the endoscopic insertion section in some of commonly known endoscopic apparatus (see, for example, Japanese Unexamined Patent Application, First Publication No. 2004-341546).

Provided at the tip of the endoscopic insertion section of the endoscopic apparatus is a cylindrical insertion electrode section connected to a power supply section. In addition, an adapter electrode section connected to the lighting section is provided to the endoscope adapter. The adapter electrode section is provided with a round electrode terminal disposed in an attaching hole having a compression spring. The electrode terminal is disposed movably along the longitudinal direction of the attaching hole so as to extend from and retract into the opening section of attaching hole. Attaching the endoscope adapter onto the tip of the endoscopic insertion section electrically connects the adapter electrode section to an insertion electrode section, thus supplying electric power from the power supply section to the lighting section.

Formed on the tip of the endoscopic insertion section of the endoscopic apparatus is an attaching surface onto which the adapter is attached. The attaching surface has a cylindrical electrode thereon which is connected to the power supply system. Also, the adapter has an electrode connected to the lighting section, etc. Attaching consequently the adapter onto the tip of the endoscopic insertion section electrically connects the electrode disposed to the adapter and the electrode disposed to the insertion section, thereby supplying electric power to the lighting section.

It is an object of the present invention to provide an endoscopic apparatus and an endoscope adapter having an endoscope adapter and an endoscopic insertion section not so significant in sizes; being capable of closing an opening section in a state where the endoscope adapter is attached to the endoscopic insertion section; and being capable of maintaining the electrode terminal clean for a prolonged period.

SUMMARY OF THE INVENTION

The present invention provides the following components.

A first aspect of the present invention is an endoscope adapter for use with an endoscope. The endoscope includes an endoscopic insertion section subject to be inserted into an object subject to inspection and the endoscope adapter so that the endoscopic insertion section has an insertion section electrode; the endoscope adapter comprises a lighting section for emitting light to the object and an adapter electrode section connected to the lighting section. The adapter electrode section comprises: an elongated hollow casing having an opening section at one end in the longitudinal direction of the casing; and a columnar electrode terminal configured to be movable in the longitudinal direction in the hollow casing and capable of projecting from the longitudinal direction end of the hollow casing. The inner diameter of the opening section is equalized to the outer diameter of the electrode terminal.

Attaching the endoscope adapter to the endoscopic insertion section in the endoscope adapter according to the present invention thrusts the electrode terminal innermore toward the endoscope adapter. The electrode terminal having a columnar shape maintains the constant distance between the inner wall of the opening section and the exterior wall of the electrode terminal irrespective of position of the electrode terminal in the longitudinal direction as long as the electrode terminal is disposed within the opening section. Equalizing the inner diameter of the opening section to the outer diameter of the electrode blocks the interspace between the inner wall of the opening section and the exterior wall of the electrode terminal irrespective of the position of the electrode terminal in the longitudinal direction.

This prevents the occurrence of an interspace between the inner wall of the opening section and the exterior wall of the electrode terminal when coupled to the endoscopic insertion section. Accordingly, this prevents dust from entering and sticking to the inside of the adapter electrode section.

In a second aspect of the present invention, one of the adapter electrode section and the insertion electrode section is provided with the hollow casing and the electrode terminal, and the electrode terminal is configured to be movable in the longitudinal direction in the hollow casing and capable of projecting from the longitudinal direction end of the hollow casing.

In the endoscopic apparatus according to the present invention, detaching the endoscope adapter from the endoscopic insertion section projects the electrode terminal from one longitudinal end of the hollow casing, and coupling the endoscope adapter to the endoscopic insertion section thrusts the electrode terminal toward the adapter electrode section or the insertion electrode section, thereby moving the electrode terminal innermore toward the hollow casing.

This provides a reliable connection between the adapter electrode section and the insertion electrode section when the endoscope adapter is coupled to the endoscopic insertion section.

In a third aspect of the present invention, the hollow casing of the endoscopic apparatus is electrically conductive.

Electrical power can be efficiently supplied to the lighting section disposed in the endoscope adapter since the hollow casing of the endoscopic apparatus according to the present invention is electrically conductive.

In a fourth aspect of the present invention, an attaching section subject to attaching to the hollow casing is provided to one of the endoscope adapter and the endoscopic insertion section, and the adapter further has an insulative unit for insulating the hollow casing from the attaching section.

The insulative unit isolates the hollow casing from the attaching section in the endoscopic apparatus according to the present invention.

This reduces the electrical loss in the adapter electrode section or the insertion electrode section.

A fifth aspect of the present invention is an endoscopic apparatus for use in observing an object subject to inspection. The apparatus includes: an endoscopic insertion section subjected to be inserted into the object subject to inspection, the endoscopic insertion section having insertion section electrodes; and an endoscope adapter having an adapter electrode section electrically connected to a lighting section for emitting light to the object, the endoscope adapter being subjected to being detachably attached to the endoscopic insertion section. The endoscopic insertion section is provided with an insertion electrode section electrically connected to the adapter electrode section when the endoscope adapter is attached to the endoscopic insertion section. The insertion electrode section includes: an elongated hollow casing having an opening section at one end in the longitudinal direction of the casing; and a columnar electrode terminal configured to be movable in the longitudinal direction in the hollow casing and capable of projecting from the longitudinal direction end of the hollow casing, and the inner diameter of the opening section is equalized to the outer diameter of the electrode terminal.

Attaching the endoscope adapter of the endoscopic apparatus to the endoscopic insertion section electrically connects the adapter electrode section to the insertion electrode section. In this state, the electrode terminal is thrusted by the adapter electrode section innermore toward the endoscopic insertion section. The electrode terminal having a columnar shape maintains the constant distance between the inner wall of the opening section and the exterior wall of the electrode terminal irrespective of position of the electrode terminal in the longitudinal direction as long as the electrode terminal is disposed within the opening section. Equalizing the inner diameter of the opening section to the outer diameter of the electrode blocks the interspace between the inner wall of the opening section and the exterior wall of the electrode terminal irrespective of the position of the electrode terminal in the longitudinal direction.

This prevents the occurrence of an interspace between the inner wall of the opening section and the exterior wall of the electrode terminal when the endoscope adapter is coupled to the endoscopic insertion section. Accordingly, this prevents dust from entering and sticking to the inside of the insertion electrode section.

As sixth aspect of the present invention is an endoscopic apparatus including: an endoscopic insertion section subjected to be inserted into an object subject to inspection; an attaching surface disposed to the endoscopic insertion section, the surface being subjected to be detachably attached to the adapter having the adapter electrode section; and the insertion section electrode disposed to the endoscopic insertion section, the electrode being subjected to being electrically connected to the adapter electrode section when the adapter is attached to the attaching surface. The insertion section electrode is disposed innermore toward the endoscopic insertion section relative to the attaching surface.

In the endoscopic apparatus according to the present invention, attaching the adapter to the attaching surface of the endoscopic insertion section electrically connects the insertion section electrode to the adapter electrode. On the other hand, the insertion section electrode detached therefrom is concealed from the surface of the attaching surface since the insertion section electrode is disposed innermore relative to the attaching surface.

This prevents the insertion section electrode from projecting relative to the attaching surface when the adapter is detached from the endoscopic insertion section.

In a seventh aspect of the present invention, a recess accommodating the insertion section electrode is formed in the attaching surface.

Accordingly, the insertion section electrode is reliably prevented from projecting from the surface of the attaching surface in the endoscopic apparatus according to the present invention since the insertion section electrode is disposed in the recess.

An eighth aspect of the present invention is an endoscopic apparatus including: an endoscopic insertion section subjected to be inserted into an object subject to inspection; an attaching surface disposed to the endoscopic insertion section, the surface being subjected to being detachably attached to the adapter having the adapter electrode section; and the insertion section electrode disposed to the endoscopic insertion section, the electrode being subjected to being electrically connected to the adapter electrode section when the adapter is attached to the attaching surface; and projecting sections disposed in the vicinity of the insertion section electrode on the attaching surface and projecting from the attaching surface. The insertion section electrode is disposed innermore toward the attaching surface relative to the tip of the projecting sections.

In the endoscopic apparatus according to the present invention, attaching the adapter to the attaching surface of the endoscopic insertion section electrically connects the insertion section electrode to the adapter electrode. On the other hand, at least a portion of the insertion section electrode is concealed by the projecting sections when the adapter is detached since the insertion section electrode is disposed closer to the attaching surface than the tip of the projecting sections.

This prevents the projection of the insertion section electrode when the adapter is detached from the endoscopic insertion section.

In a ninth aspect of the present invention, the projecting sections are provided with a hollow section extending in the projecting direction, the insertion section electrode being disposed in the hollow section.

Accordingly, the insertion section electrode is reliably prevented from projecting from the surface of the attaching surface in the endoscopic apparatus according to the present invention since the insertion section electrode is disposed in the recess.

DETAILED DESCRIPTION OF THE INVENTION (Embodiment 1)

An endoscopic apparatus according to a first embodiment of the present invention will be explained with reference to the attached drawings.

Figure 1:
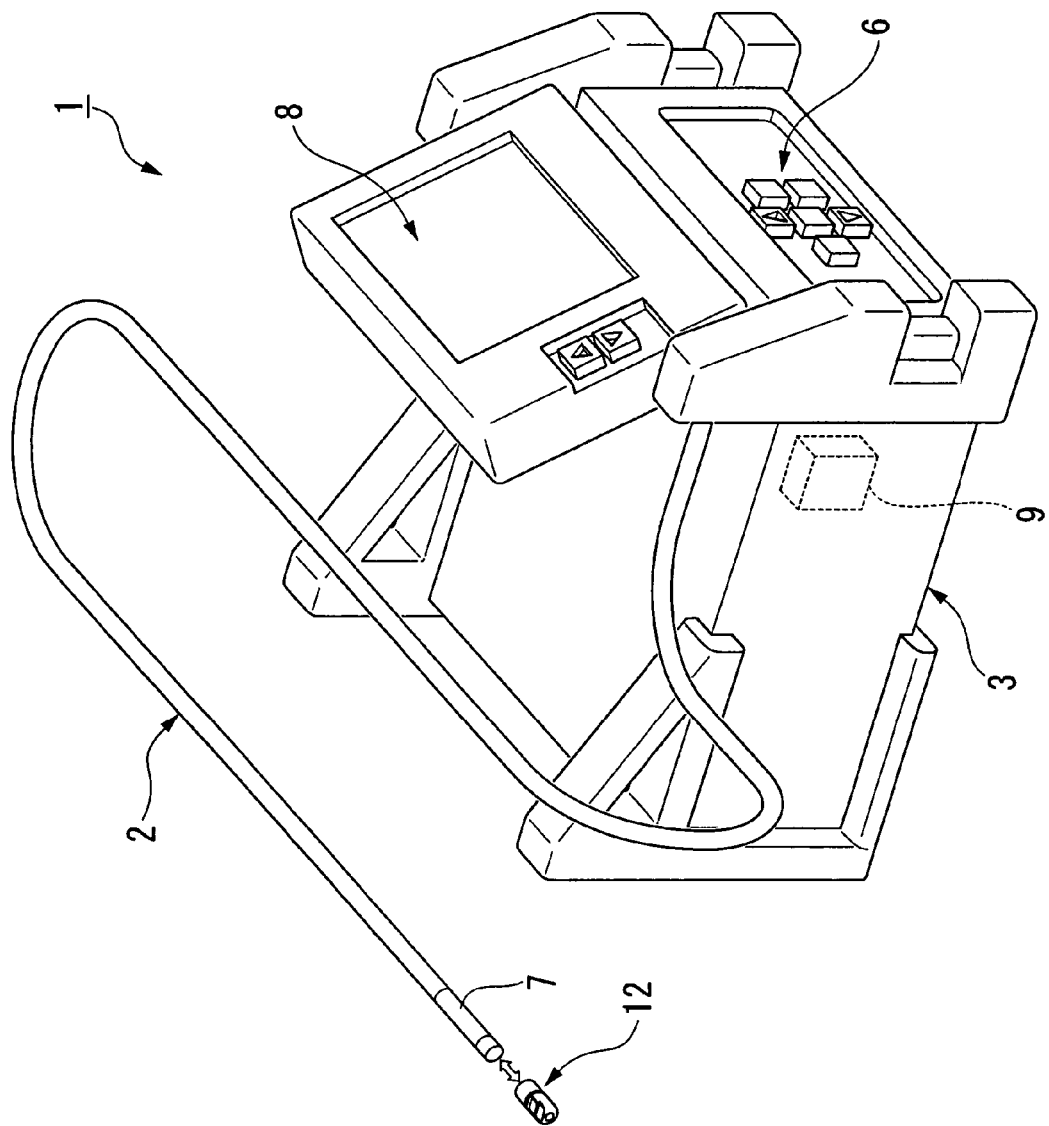
FIG. 1 illustrates first and fifth embodiments of the endoscopic apparatus according to the present invention in a schematic view.

FIG. 1 illustrates the endoscope device according to the first embodiment of the present invention.

An endoscope apparatus 1 is provided with an insertion section 2 (endoscopic insertion section) having a bending section 7 capable of bending; and a main body section 3 variously operable when used with the insertion section 2 inserted thereinto.

The approximately box-shaped main body section 3 has a side wall section onto which an operation panel 6 used for carrying out various operations is disposed. In addition, a monitor 8 for exhibiting an observed image is disposed on a ceiling of the main body section 3. Furthermore, a power supply section 9 for supplying electric power is disposed to the main body section 3.

Figure 2:
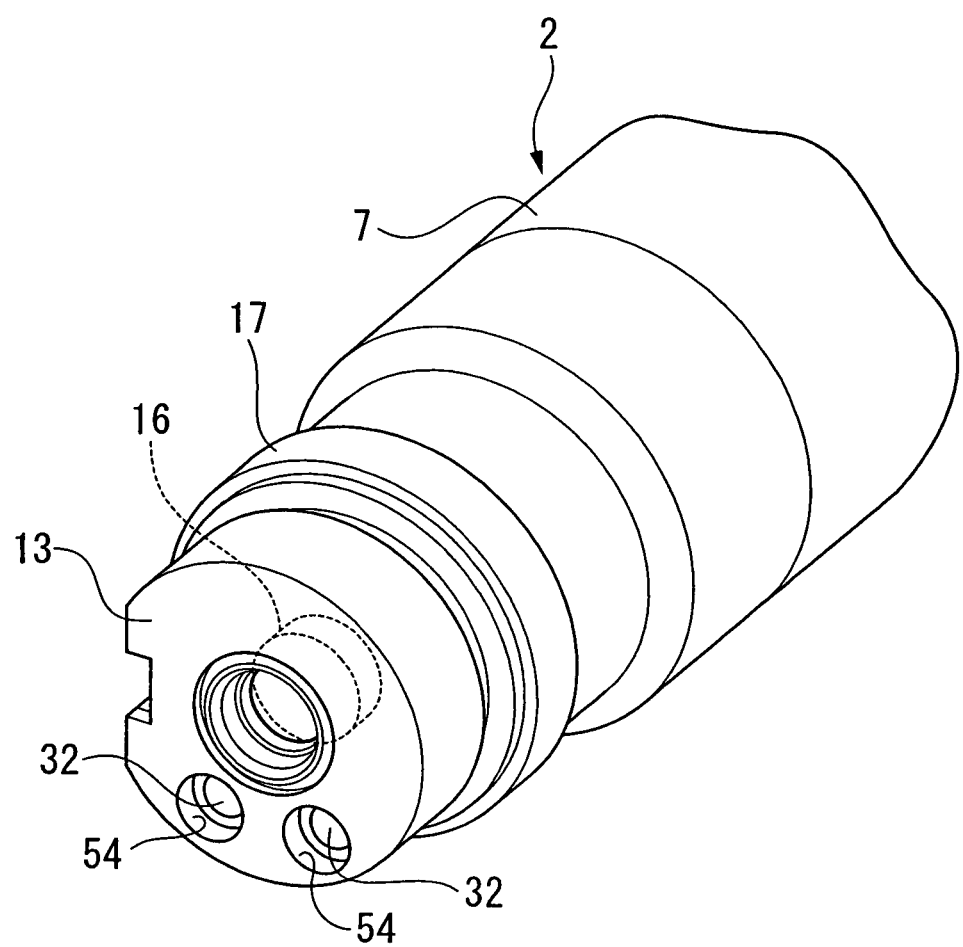
FIG. 2 illustrates the tip of the insertion section of the endoscopic apparatus of FIG. 1 in an enlarged perspective view.

Also, the base end section of the insertion section 2 is configured to be detachably attached to the main body section 3 through a connecting section which is not shown in the drawings. Meanwhile an observing unit using a CCD 16 is disposed onto the tip thereof as shown in FIG. 2. In addition, a fitting-protrusion section 17 is disposed over the circumference of the insertion section 2 while protruding outwardly in a radial direction. An insertion section-mounting surface 13 is disposed on the tip of the insertion section 2 so that an optical adapter 12 (shown in FIG. 1) having an object lens which is not shown in the drawing is detachably attached onto the surface 13. Fixed onto the insertion section-mounting surface 13 is an insertion section electrode section 32 which is electrically connected to the power supply section 9 shown in FIG. 1. The insertion section electrode section 32 will be explained afterwards.

Figure 3:
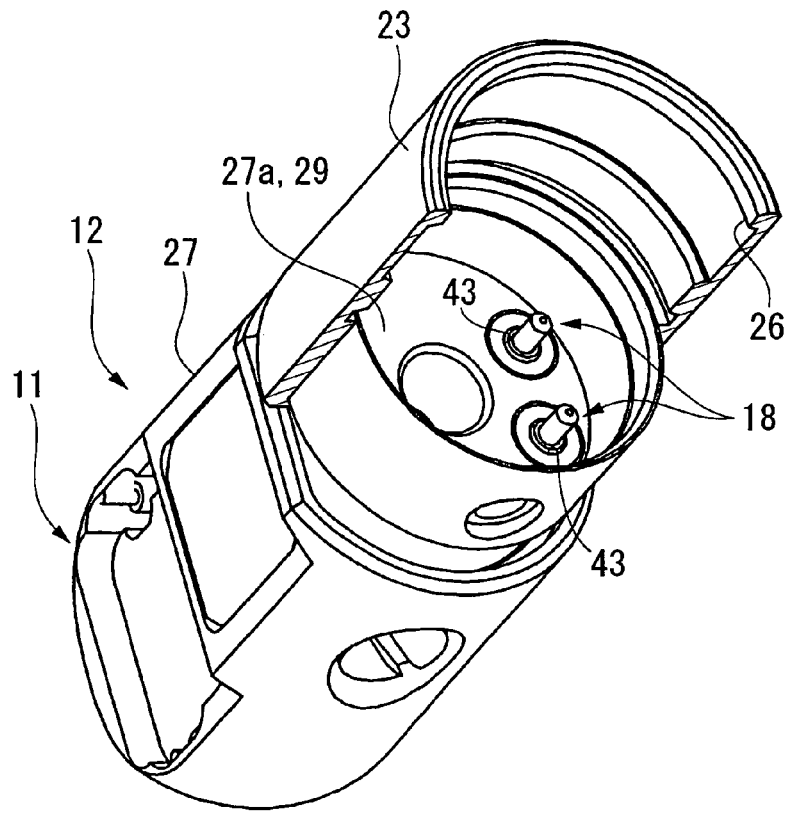
FIG. 3 is an enlarged view of the optical adapter shown in FIG. 1 viewed from the base end including an attaching hood approximately half of which is illustrated in a cutout view.

As illustrated in FIG. 3, the optical adapter (endoscope adapter) 12 is provided with an adapter main body 27 having an approximate columnar shape; and an attachment hood section 23 having an approximate cylindrical shape and being coaxially joined to the base end of the adapter main body 27.

Provided onto the side wall section of the adapter main body 27 is a lighting section 11 having, for example LEDs. In addition, formed on the bottom surface section 27a of the adapter main body 27 is an adapter-mounting surface 29 by way of which the optical adapter 12 is attached to the insertion section 2. Provided onto the adapter-mounting surface 29 is a movable adapter electrode section 18 electrically connected to the lighting section 11. The adapter electrode section 18 will also be explained afterwards.

Furthermore, formed on the inner periphery of the attachment hood section 23 is a mounting groove 26 extending over the circumference of the hood 23.

Squeezing the optical adapter 12 into the insertion section-mounting surface 13 as shown in FIG. 2 fits the fitting-protrusion section 17 with the mounting groove 26, and this configuration allows detachable attaching of the optical adapter 12 onto the tip of the insertion section 2 while maintaining the insertion section-mounting surface 13 to face the adapter-mounting surface 29.

Figure 4:
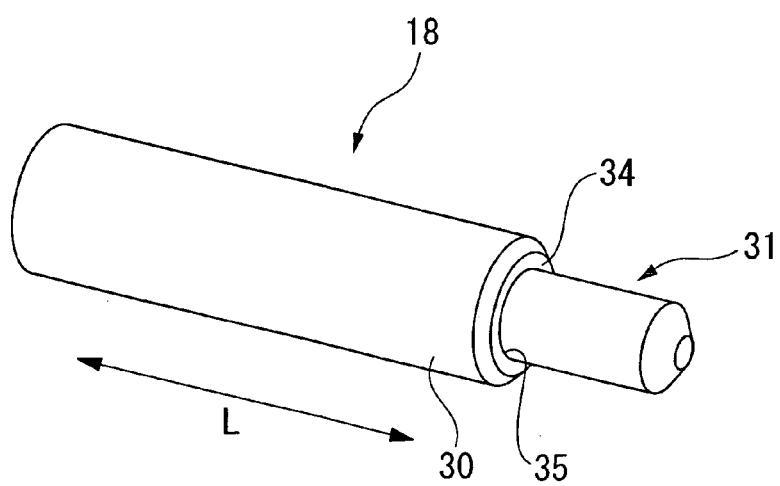
FIG. 4 illustrates the adapter electrode section of FIG. 3 in an enlarged perspective view.
Figure 5:
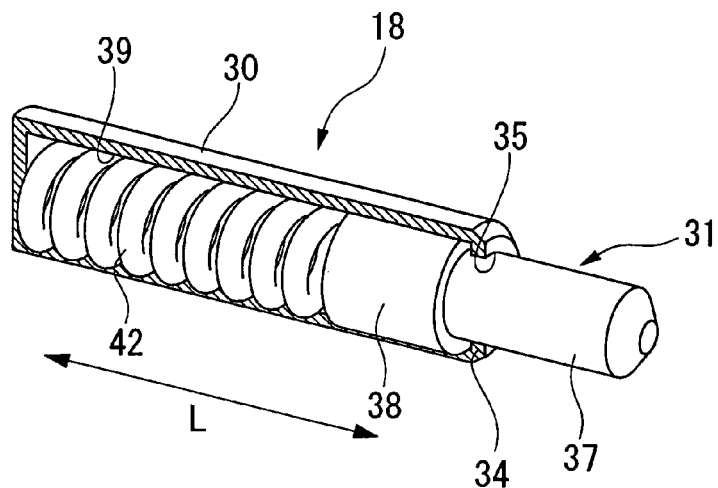
FIG. 5 is a half-cutaway view of a hollow casing shown in FIG. 4.

Furthermore, as shown in FIGS. 4 and 5, the adapter electrode section 18 according to the present embodiment is provided with a hollow casing 30 having a bottom section and a cylindrical section and an approximate columnar electrode terminal 31.

The hollow casing 30 possesses electrical conductivity and is made from nonferrous metals and ferrous metals, e.g., iron. In addition, an inward flange section 34 formed on one end of the hollow casing 30 in a longitudinal direction L is inwardly directed in a radial direction of the casing 30. Crimping the end of the hollow casing 30 provides the inward flange section 34. The inward flange section 34 also defines a circular opening section 35 on the end of the hollow casing 30.

Also, highly conductive plating or painting is applied to the surface of the electrode terminal 31 made of metal. The electrode terminal 31 is further provided with a columnar terminal tip section 37 and a terminal base end section 38. The terminal tip section 37 is coaxially jointed to the terminal base end section 38 in one unit. The terminal tip section 37 projects from the hollow casing 30 through the opening section 35 formed at the end of the casing 30. The inner diameter of the opening section 35 is set to be the same as the outer diameter of the terminal tip section 37, so disposing the terminal tip section 37 into the opening section 35 blocks the opening section 35.

It should be noted that, in the present invention, the same dimensions with respect to the inner diameter of the opening section and the outer diameter of the tip of the terminal indicate that there is a clearance that allows the tip of the terminal to slidably move through the opening section.

Also, the terminal base end section 38 greater than the terminal tip section 37 in diameter is configured to slidably move in the tubular hole 39 (hollow casing) of the hollow casing 30 in the longitudinal direction L. The movement of the terminal base end section 38 in the tubular hole 39 allows the terminal tip section 37 to project from and retract into the opening section 35 formed at the end of the hollow casing 30. Furthermore, the terminal base end section 38 makes contact with the inward flange section 34 before the terminal base end section 38 moves out of the opening section 35. That is, the inward flange section 34 works as a retainer against the electrode terminal 31.

Provided between the terminal base end section 38 and the bottom section inside the hollow casing 30 is a coil spring (urging member) 42. The force exerted by the coil spring 42 presses the terminal base end section 38 at the end of the hollow casing 30, thereby maintaining the terminal tip section 37 to project outward from the end of the hollow casing 30. The coil spring 42 is made from electrically conductive metal.

Figure 6:
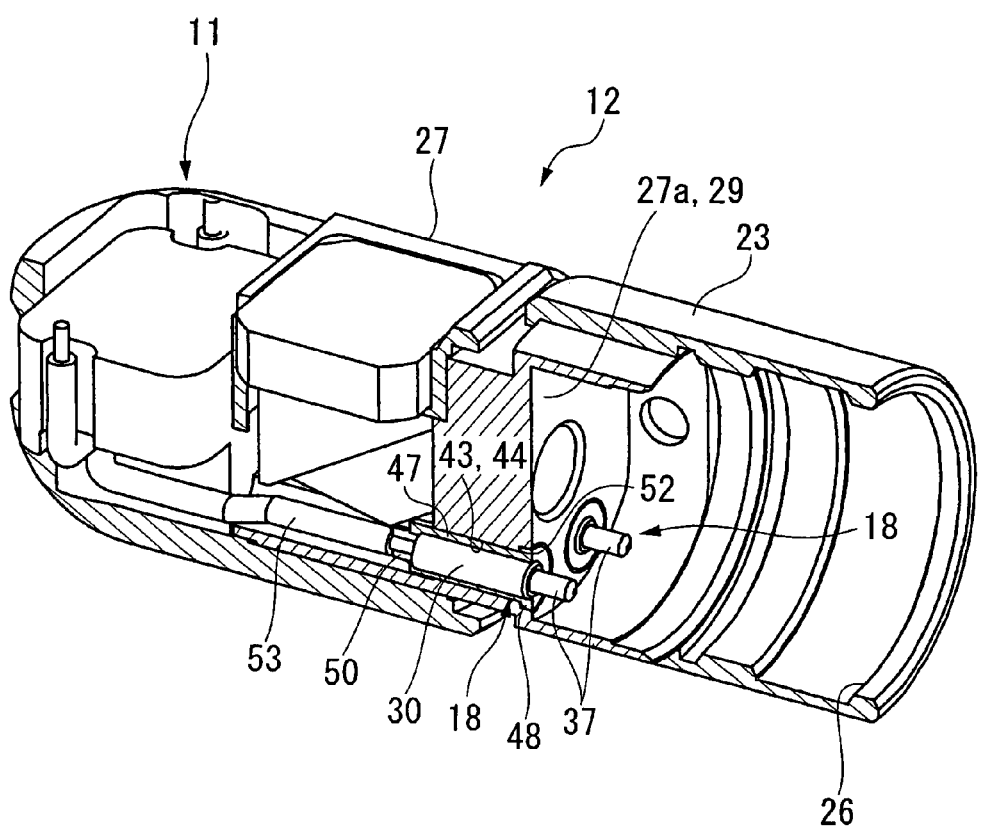
FIG. 6 is a half-cutaway view of a hollow casing shown in FIG. 3.
Figure 7:
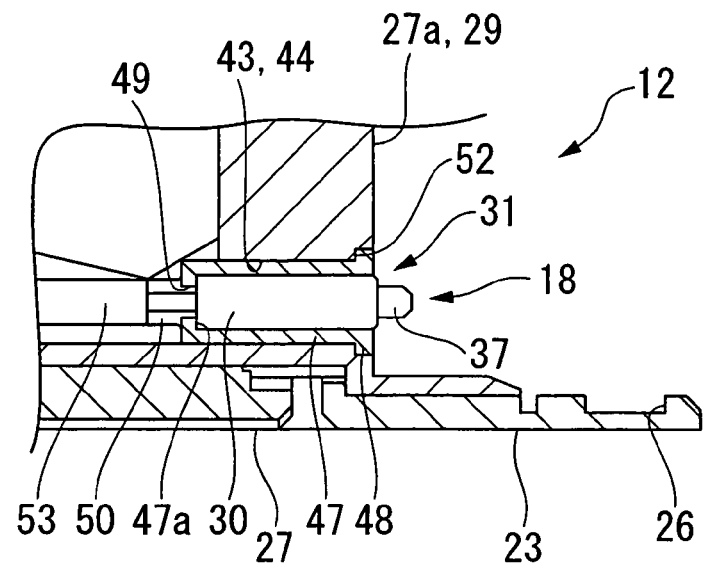
FIG. 7 illustrates the substantial peripheral part of the adapter electrode section shown in FIG. 6 in a cross sectional view.

In this configuration, provided further around the adapter electrode section 18 is an insulative casing (insulative unit) 47 surrounding the hollow casing 30 as shown in FIGS. 6 and 7. To be more specific, the insulative casing 47 has a bottom section, a cylinder section, and a cylindrical hole into which the adapter electrode section 18 is inserted and fixed there. The bottom surface of the hollow casing 30 makes contact with the bottom surface section 47a of the insulative casing 47. Formed at the end of the insulative casing 47 is a flange section 48 extending outward in the radial direction of the insulative casing 47. A through hole 49 is formed in the center of the bottom surface section 47a of the insulative casing 47.

The endoscope adapter is inserted into the insulative casing 47 inserted in the adapter electrode section 18 is attached in the electrode-mounting hole 43 formed in the optical adapter 12. That is, the inner peripheral wall section 44 defining the electrode-mounting hole 43 works as an attaching portion accommodating the hollow casing 30 and the insulative casing 47 thereon. The terminal tip section 37 projects from the adapter-mounting surface 29 while the adapter electrode section 18 is mounted in the electrode-mounting hole 43.

A portion of the bottom surface section 27a disposed at one longitudinal end of the inner peripheral wall section 44 has a step section 52 with which the outward-extending flange section 48 makes contact.

The force needed to push the adapter electrode section 18 into the optical adapter 12 is supported by the bottom surface section 47a of the insulative casing 47, thereby restraining the movement of the hollow casing 30 inward, i.e., toward the inside of the optical adapter 12 in this configuration. Furthermore, the force pushing the insulative casing 47 into the optical adapter 12 is supported by the step section 52, thereby restraining the movement of the insulative casing 47 into the optical adapter 12. That is, the bottom surface section 47a of the insulative casing 47 serves for restraining the movement of the hollow casing; and the step section 52 and the outward-extending flange section 48 serve for restraining the movement of the insulative member.

The insulative casing 47 furthermore serves for providing insulation to the hollow casing 30 and the inner peripheral wall section 44.

An end of a cable 53 inserted through the through hole 49 into the insulative casing 47 is electrically soldered to the outer surface of the bottom of the hollow casing 30. The other end of the cable 53 is electrically connected to the lighting section 11. Reference numeral 50 indicates the soldered portion.

As shown in FIG. 2, the insertion section-mounting surface 13 of the insertion section 2 furthermore has recesses 54 accommodating insertion section electrode sections 32 each having a bottom and a cylinder section. The innermost section of each insertion section electrode section 32 is bent inner more in the radial direction than the recess 54. To be more specific, each insertion section electrode section 32 subsides inward of the insertion section 2 relative to the insertion section-mounting surface 13. Each insertion section electrode section 32 is concealed from the insertion section-mounting surface 13 by a sidewall section of the recess 54. Also, highly conductive plating or painting is applied to the surface of the insertion section electrode section 32 made of metal.

The operation of the endoscope apparatus 1 thus configured in the present embodiment will be explained next.

The optical adapter 12 is first attached onto the insertion section-mounting surface 13 of the insertion section 2. The terminal tip section 37 is subsequently disposed in the recess 54 and makes contact with the outer surface of the bottom of the insertion section electrode section 32. This electrically connects the adapter electrode section 18 to the insertion section electrode section 32, thereby supplying electric power to the lighting section 11 from the power supply section 9. The lighting section 11 of the insertion section 2 introduced into an object subject to inspection emits light. The light reflected by the object subject to inspection passes through object lenses in the optical adapter 12 and an image thereof is formed on a CCD 16. A signal output from the CCD 16 is supplied to a monitor 8 through a predetermined circuit. This provides an observed image exhibited on the monitor 8 used for a predetermined inspection of the object.

The adapter electrode section 18 is electrically connected to the insertion section electrode section 32 upon coupling the optical adapter 12 to the insertion section-mounting surface 13.

To be more specific, the optical adapter 12 is brought to the tip of the insertion section 2 and pushed thereinto while the insertion section-mounting surface 13 faces the adapter-mounting surface 29. The terminal tip section 37 is subsequently disposed in the recess 54 and makes contact with the insertion section electrode section 32. Pushing furthermore the optical adapter 12 thereinto causes the insertion section electrode section 32 to press the terminal tip section 37 innermore toward the optical adapter 12. The terminal tip section 37 moves in the subsiding direction into the hollow casing 30 through the opening section 35. Simultaneously, the terminal base end section 38 resisting the force exerted by the coil spring 42 moves in the hollow casing 30 into the optical adapter 12.

The constant interspace is maintained between the exterior wall of the terminal tip section 37 and the inner wall of the opening section 35 when the cylindrical terminal tip section 37 moves into the hollow casing 30 through the opening section 35. Configuring the outer diameter of the terminal tip section 37 to be the same as the inner diameter of the opening section 35 blocks the interspace between the exterior wall of the terminal tip section 37 and the inner wall of the opening section 35 irrespective of the position of the terminal tip section 37.

The fitting-protrusion section 17 of the insertion section 2 fits with a mounting groove 26 while the terminal tip section 37 is depressed; thus, the optical adapter 12 is attached onto the tip of the insertion section 2. The projection of the terminal tip section 37 in length from the adapter-mounting surface 29 through the opening section 35 reduces according to the depression caused by the insertion section electrode section 32. The terminal tip section 37 is further pressed toward the insertion section electrode section 32 by the force exerted by the coil spring 42. The contact between the terminal tip section 37 and the insertion section electrode section 32 is therefore maintained. This configuration allows the adapter electrode section 18 to be electrically connected to the insertion section electrode section 32.

Although the hollow casing 30 and the insulative casing 47 subject to the pressing force are apt to move into the optical adapter 12 when the optical adapter 12 is attached onto the tip of the insertion section 2, the movements of these casings 30 and 47 are restrained by making contacts with the bottom surface section 47a of the insulative casing 47 and the step section 52.

Since the interspace between the exterior wall of the terminal tip section 37 and the inner wall of the opening section 35 can be continuous irrespective of the position of the terminal tip section 37 in the endoscope apparatus 1, the present embodiment does not allow the interspace between the exterior wall of the terminal tip section 37 and the inner wall of the opening section 35 while the optical adapter 12 is attached to the insertion section 2.

This prevents dust from entering and sticking inside of the adapter electrode section 18. Poor contact can be prevented accordingly, thus the cleanness of the adapter electrode section 18 can be maintained in the long term. Also preventing the entry of dust reduces the cleaning cycle; thus facilitating regular care.

The circular shapes of the opening section 35 and the terminal tip section 37 not only allow smooth movement of the terminal tip section 37 through the opening section 35 but provide a uniform block between the inner wall of the opening section 35 and the exterior wall of the terminal tip section 37.

The terminal tip section 37 mounted in the hollow casing 30 through the opening section 35 is pushed by the force exerted by the coil spring 42; thus coupling the optical adapter 12 into the insertion section 2 results in secure connection between the adapter electrode section 18 and the insertion section electrode section 32.

The electric power supplied by the power supply section 9 can be further supplied to the lighting section 11 through the coil spring 42 and the hollow casing 30 that are electrically conductive. The efficiency thus increases in supplying electricity. Although the electrical resistance of the coil spring 42 is significant because of its insignificant cross sectional area and significant longitudinal length, insignificant electrical resistance in the hollow casing 30 having a significant cross sectional area and insignificant longitudinal length connected to the cable 53 help to efficiently supply the electric power in the present embodiment.

The isolation between the hollow casing 30 and the inner peripheral wall section 44 obtained by the insulative casing 47 can lower the electrical loss of the adapter electrode section 18.

The insertion section electrode section 32 subsides from the insertion section-mounting surface 13, i.e., is concealed from the insertion section-mounting surface 13, thereby resisting damage of the insertion section electrode section 32 and preventing dust from entering or sticking there with the optical adapter 12 detached. The cleanness of the insertion section electrode section 32 can be thus maintained effectively.

The inward flange section 34 formed to the hollow casing 30 prevents the removal of the electrode terminal 31 from the hollow casing 30 while allowing smooth movement of the electrode terminal 31.

Furthermore, the bottom surface section 47a and the step section 52 that are formed to the insulative casing 47 restrain the hollow casing 30 and the insulative casing 47 from moving inward into the optical adapter 12, thereby facilitating fixing the hollow casing 30 and the insulative casing 47 to the inner peripheral wall section 44 and maintaining suitable contact between the adapter electrode section 18 and the insertion section electrode section 32 in the long term.

Also coupling the optical adapter 12 to the insertion section 2 connects the the radially-inner surface of the insertion section electrode section 32 to an end surface of the terminal tip section 37, thereby providing an interfacial contact between the insertion section electrode section 32 and the adapter electrode section 18. The electrical conductivity between the insertion section electrode section 32 and the adapter electrode section 18 can be obtained in the case of lower component quality or lower assembly accuracy.

The highly conductive plating or painting provided onto the insertion section electrode section 32 and the electrode terminal 31 lowers the electrical loss between the insertion section electrode section 32 and the adapter electrode section 18.

The hollow casing 30, electrode terminal 31, coil spring 42, and insulative casing 47 provided in the present embodiment are susceptible to modifications in arbitrary shape and material.

Figure 8:
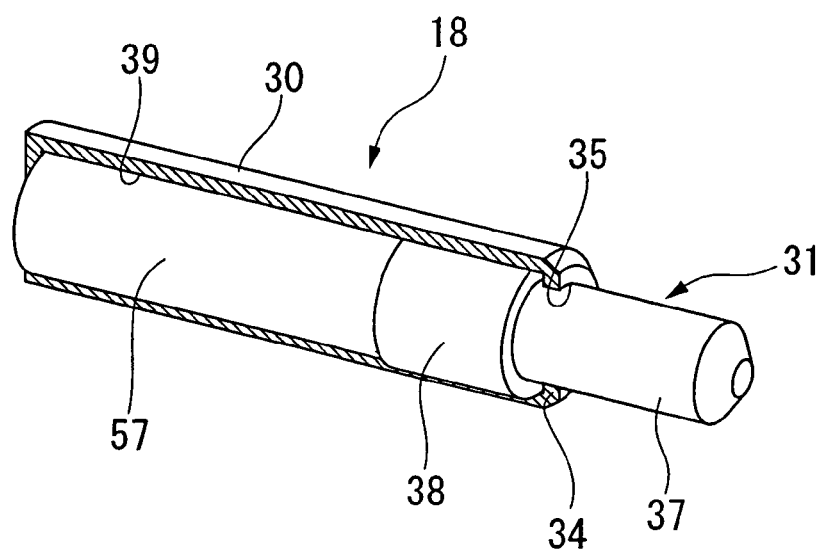
FIG. 8 illustrates a modified example of the adapter electrode section shown in FIG. 5 in a perspective view additionally having a resilient member.

For example, an elastic member (urging member) 57 may be provided as shown in FIG. 8 in place of the coil spring 42. The elastic member 57 made of conductive resin allows supplying the electrical power efficiently in an improved manner.

Figure 9:
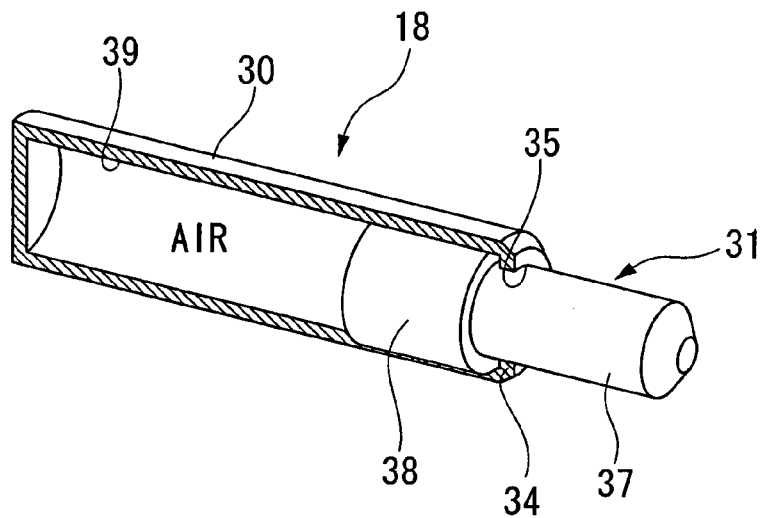
FIG. 9 illustrates another modified example of the adapter electrode section shown in FIG. 5 in a perspective view using air as a resilient member.

The configuration free of the coil spring 42 as shown in FIG. 9 may also be desirable. This case requires the hollow casing 30 to be of an airtight construction. The reciprocation of the electrode terminal 31 expands and contracts the air in the tubular hole 39, thereby rendering the air an urging member.

Figure 10:
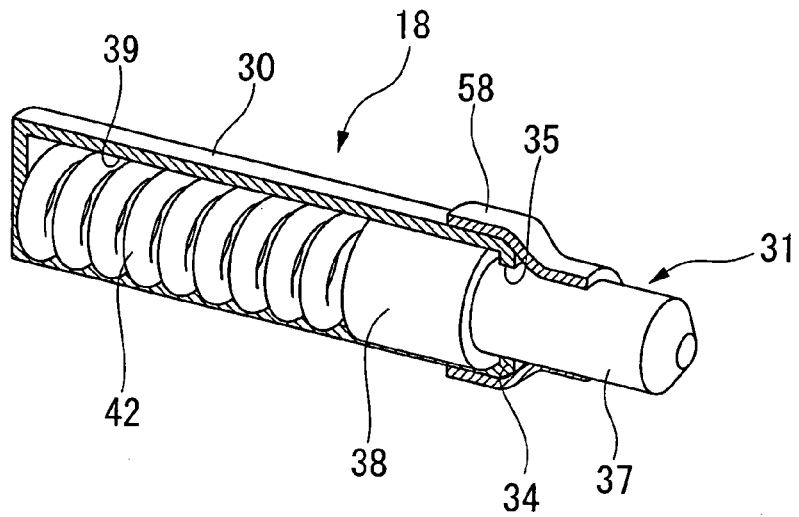
FIG. 10 illustrates another modified example of the adapter electrode section shown in FIG. 5 in a perspective view additionally having a sealing member.

Furthermore, a rubber sealing material 58 may be provided to the tip of the hollow casing 30 as shown in FIG. 10. This prevents water from entering into the adapter electrode section 18, thereby preventing corrosion and failure due to the submergence.

Figure 11:
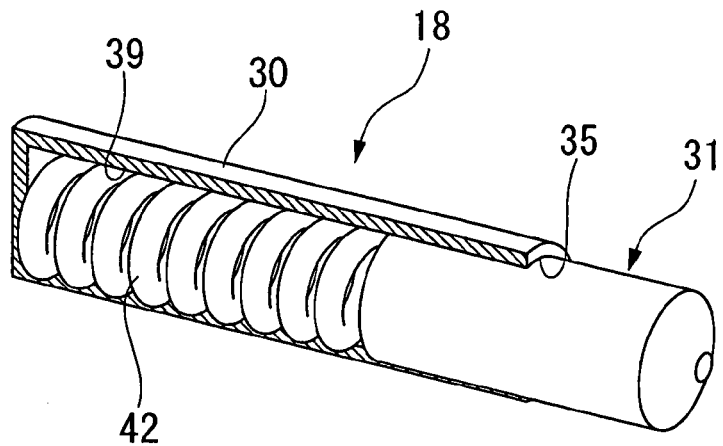
FIG. 11 illustrates another modified example of the adapter electrode section shown in FIG. 5 in a perspective view additionally having a columnar electrode terminal.

The electrode terminal 31 may be a column having an identical diameter over the longitudinal length as shown in FIG. 11. This facilitates the production of the electrode terminal 31. This case requires to fix the tip of the coil spring 42 to the rear end of the electrode terminal 31 and to fix the rear end of the coil spring 42 to the inner bottom surface of the hollow casing 30. This configuration eliminates the need of the inward flange section 34, thereby simplifying the configuration.

Figure 12:
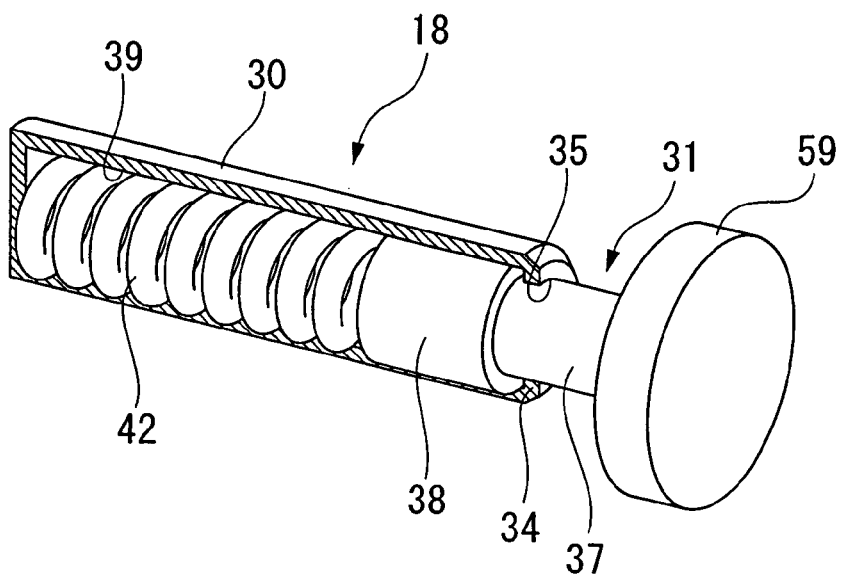
FIG. 12 illustrates another modified example of the adapter electrode section shown in FIG. 5 in a perspective view additionally showing a large diameter portion at the tip of the terminal.

A large-diameter tip section 59 having a larger diameter than that of the terminal tip section 37 may be formed at the tip of the terminal tip section 37 as shown in FIG. 12. This provides contact between the large-diameter tip section 59 and the insertion section electrode section 32, thereby increasing the area contacting the insertion section electrode section 32. Therefore, superior conductivity can be obtained between the adapter electrode section 18 and the insertion section electrode section 32 in the case of lower component quality or lower assembly accuracy.

Figure 13:
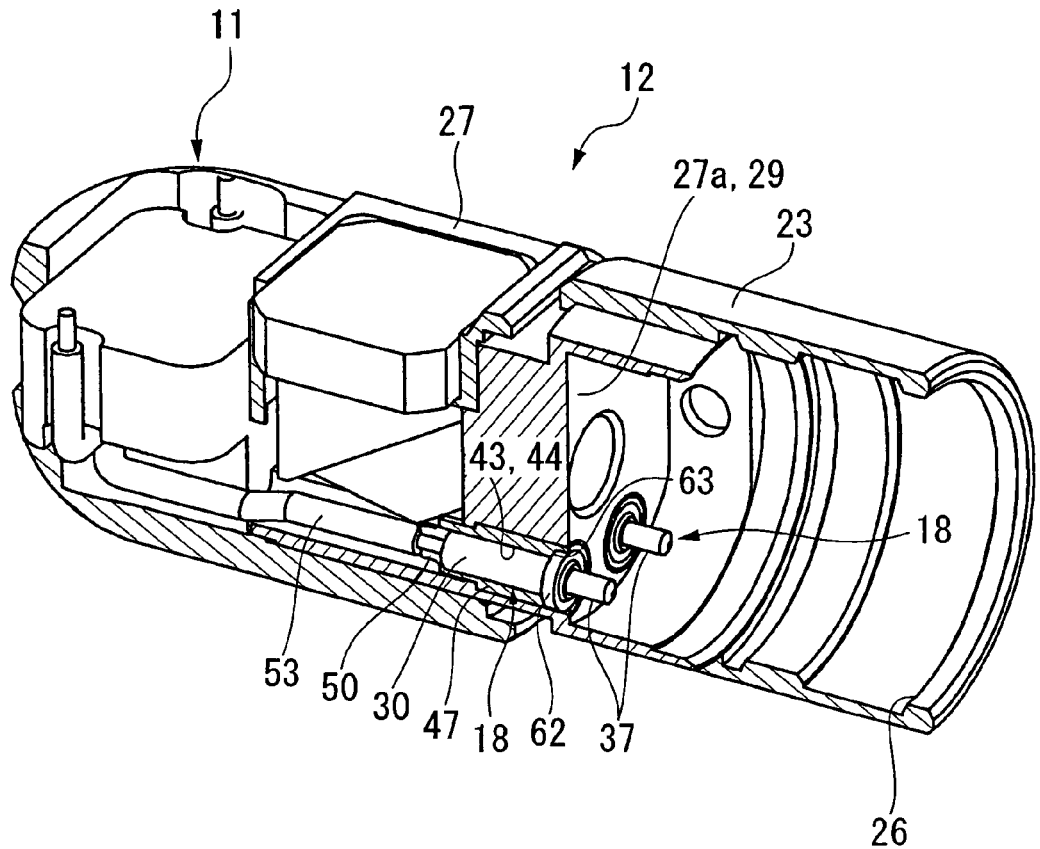
FIG. 13 illustrates modified examples of the hollow casing, the insulative casing, and inner peripheral wall section shown in FIG. 6 where an outward flange section is disposed to the hollow casing.
Figure 14:
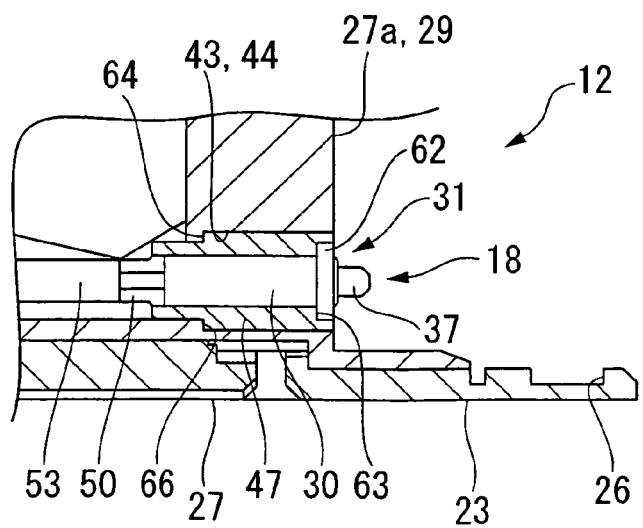
FIG. 14 illustrates the substantial peripheral part of the adapter electrode section shown in FIG. 13 in a cross sectional view.

Furthermore, as shown in FIGS. 13 and 14, an outward flange section 62 may be provided to the tip of the hollow casing 30, and a step section 63 contacting the outward flange section 62 may be provided to the tip of the insulative casing 47. The outward flange section 62 and the step section 63 serve for restraining the movement of the hollow casing. Also, an engagement step section 64 is disposed in the vicinity of the base end section of the insulative casing 47; and a counter-engagement step section 66 engaging the engagement step section 64 is formed to the inner peripheral wall section 44 near a coupling part. The engagement step section 64 and the counter-engagement step section 66 serve for restraining the movement of the insulative component.

Figure 15:
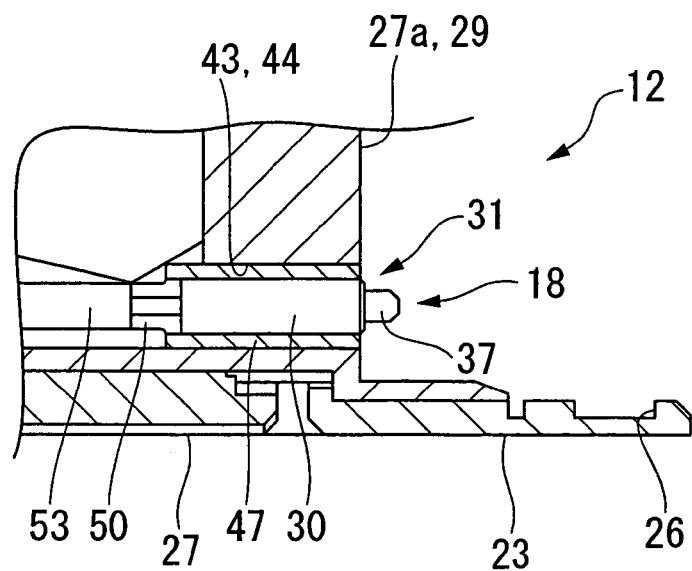
FIG. 15 illustrates modified examples of the hollow casing, the insulative casing, inner peripheral wall section that are shown in FIG. 14, and the substantial peripheral part of the adapter electrode section.

Furthermore, the insulative casing 47 may be cylindrical and the hollow casing 30 may have a bottom section and a cylinder section as shown in FIG. 15 in place of providing a step section or an outer flange section to the inner peripheral wall section 44, insulative casing 47, and hollow casing 30. This case requires the insulative casing 47 to be fixed to the hollow casing 30 using adhesives, etc.

Figure 16:
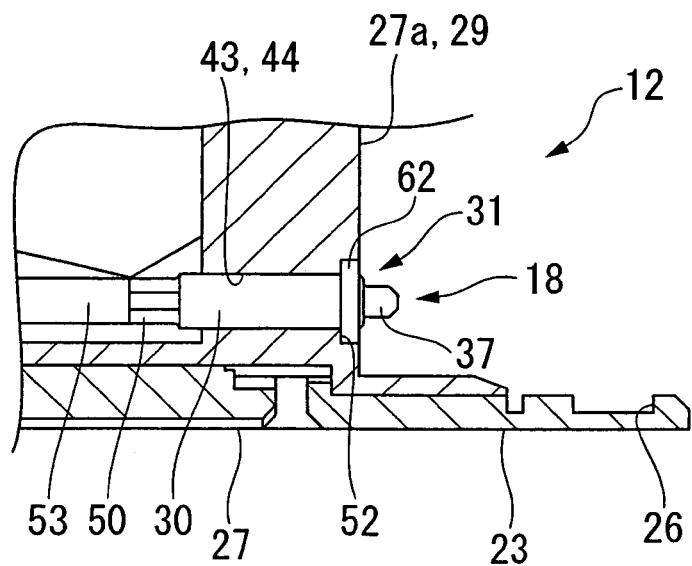
FIG. 16 illustrates other modified examples of the hollow casing, the insulative casing, inner peripheral wall section that are shown in FIG. 14, and the substantial peripheral part of the adapter electrode section.
Figure 17:
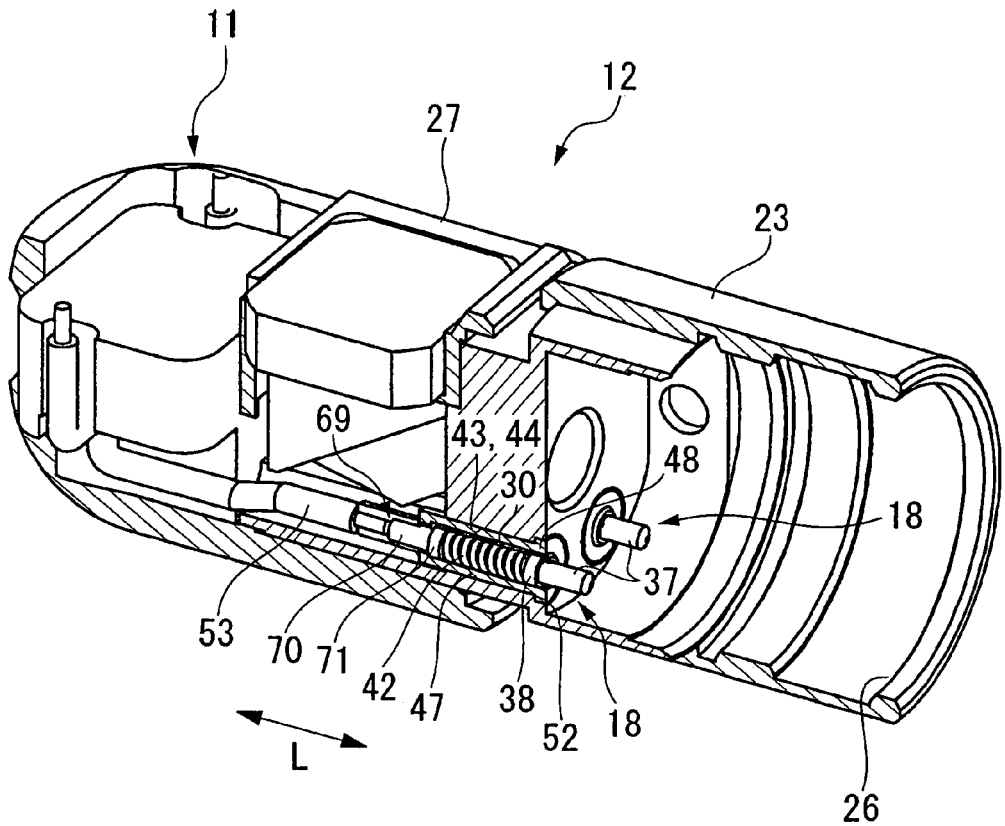
FIG. 17 illustrates modified examples of the hollow casing, the insulative casing, and inner peripheral wall section, where a counterpart terminal is disposed to the hollow casing.
Figure 18:
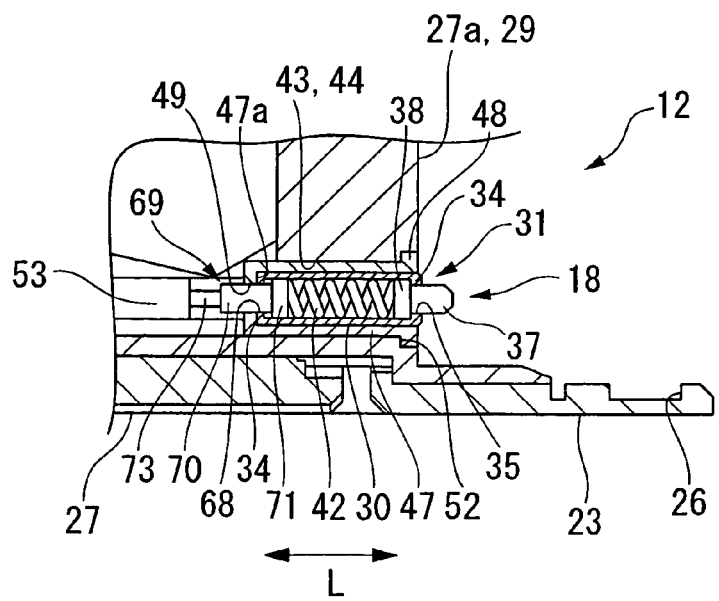
FIG. 18 illustrates the substantial peripheral part of the adapter electrode section shown in FIG. 17 in a cross sectional view.
Figure 19:
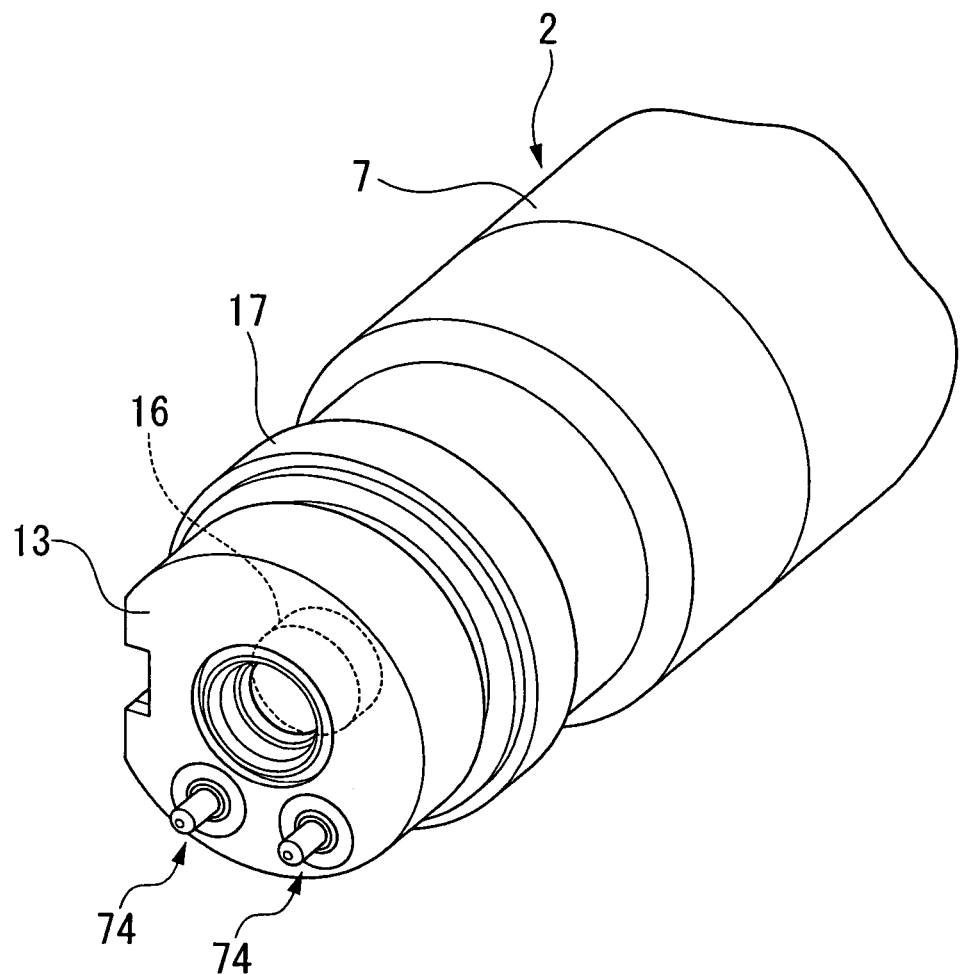
FIG. 19 shows a substantial part of the endoscopic apparatus including the tip of the insertion section according to the second embodiment of the present invention.
Figure 20:
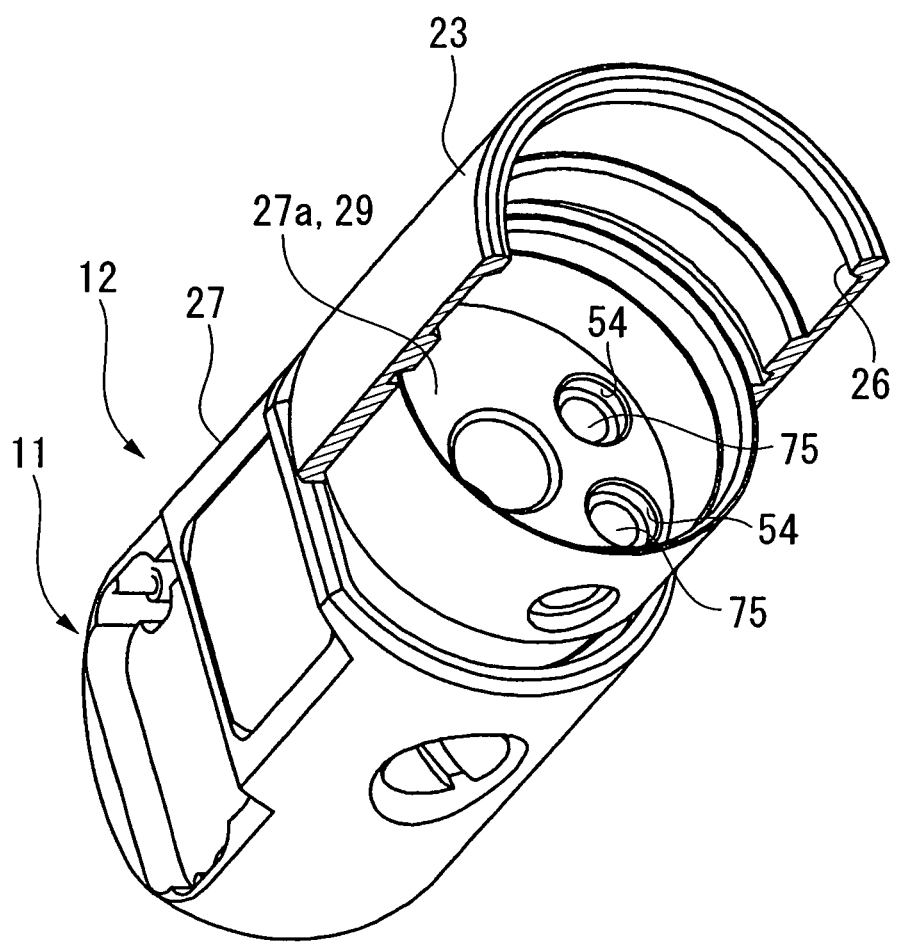
FIG. 20 shows a substantial part of the endoscopic apparatus of the second embodiment in a perspective view including a half cutaway view of the attaching hood of the optical adapter viewed from the base end.
Figure 21:
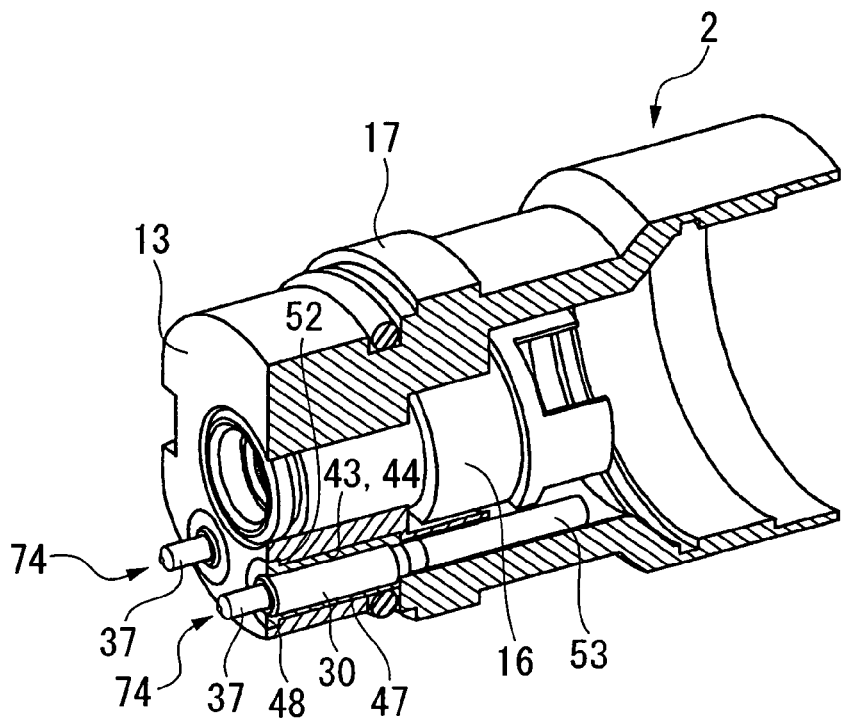
FIG. 21 is a perspective half-cutaway view of the insertion section shown in FIG. 19.
Figure 22:
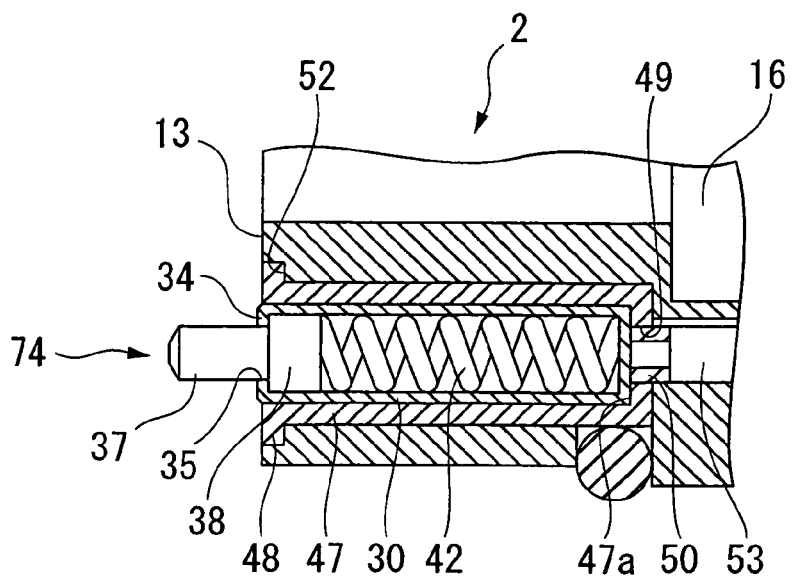
FIG. 22 illustrates the substantial peripheral part of the insertion electrode section shown in FIG. 21 in a cross sectional view.

Also, as shown in FIG. 16, the adapter electrode section 18 may be directly mounted into the inner peripheral wall section 44, i.e., without the insulative casing 47. In this case, the hollow casing 30 may be made of an insulative material, and the hollow casing 30 may be anodized so as to provide insulation on the surface thereof. In addition, the inner peripheral wall section 44 may be made of an insulative material and the surface of the inner peripheral wall section 44 may be treated to impart insulation there.

An inward flange section 34 defining the circular other counterpart opening section 68 may be provided to the other end in the longitudinal direction L of the hollow casing 30. In this case, provided to the other end of the hollow casing 30 is another columnar end terminal 69. The other end terminal 69 having a configuration similar to that of the electrode terminal 31 is provided with a columnar connection terminal section 70 and a terminal base plate section 71.

The connection terminal section 70 projects from the other end of the hollow casing 30 through the other counterpart opening section 68. The inner diameter of the other counterpart opening section 68 is set to be the same as the outer diameter of the connection terminal section 70, so disposing the connection terminal section 70 into the other counterpart opening section 68 blocks the other counterpart opening section 68. This prevents dusts from entering there through the other counterpart opening section 68.

The terminal base plate section 71 is movable in the longitudinal direction L of the tubular hole 39 in the hollow casing 30. The movement of the terminal base plate section 71 in the tubular hole 39 similarly to the electrode terminal 31 enables the reciprocation of the connection terminal section 70 from the other end of the hollow casing 30 through the other counterpart opening section 68.

The force exerted by the coil spring 42 presses the terminal base plate section 71 at the other end of the hollow casing 30, thereby urging the connection terminal section 70 outward from the other end of the hollow casing 30.

The insulative casing 47 mounted into the electrode-mounting hole 43 is configured to be detachable from the mounted condition. To be more specific, the insulative casing 47 including the adapter electrode section 18 is configured to be replaceably mounted in the electrode-mounting hole 43.

Inserting and pushing the adapter electrode section 18 into the insulative casing 47 at a predetermined position allow the connection terminal section 70 to project through the through hole 49 in this configuration. In addition, equalizing the outer diameter of the connection terminal section 70 to the inner diameter of the through hole 49 blocks the through hole 49.

Pushing the insulative casing 47 having a projecting connection terminal section 70 as described above through the connection terminal section 70 into the electrode-mounting hole 43 to the predetermined position contacts the connection terminal section 70 to the connecting section 73 disposed at the tip of the cable 53, thereby pushing the connection terminal section 70 into the hollow casing 30 while resisting the force exerted by the coil spring 42. The electrical connection between the other end terminal 69 and the connecting section 73 is maintained because the connection terminal section 70 is pushed by the force exerted by the coil spring 42 toward the connecting section 73.

In the case of failure of the adapter electrode section 18, the adapter electrode section 18 is removed together with the insulative casing 47, and another set of adapter electrode section 18 and insulative casing 47 is mounted to the inner peripheral wall section 44 as described above.

In addition, the adapter electrode section 18 may be replaceably mounted in the insulative casing 47.

The incorporation of the adapter electrode section 18 regardless of its direction is facile in the above configuration. Also, the reciprocation of the other end terminal 69 absorbs dimensional error in each component. Also, the replaceable adapter electrode section 18 facilitates repairing the optical adapter 12. The absence of necessity for fixing the other end terminal 69 to the connecting section 73 also facilitates replacing the adapter electrode section 18.

(Embodiment 2)

A second embodiment of the present invention will be next explained.

FIGS. 19 to 22 illustrate the second embodiment of the present invention.

The same reference numerals are added to the elements illustrated in FIGS. 19 to 22 that are the same as those illustrated in FIGS. 1 to 18 so as to omit duplicate explanation.

The fundamental configuration of the present embodiment is the same as that of the first embodiment; only the differences will be hereafter explained.

The adapter electrode section 18 and the insertion section electrode section 32 illustrated in the first embodiment are interchangeably disposed in the endoscope apparatus 1 of the present embodiment. To be more specific, an insertion section electrode section 74 according to the present embodiment has the same configuration as that of the adapter electrode section 18 according to the above first embodiment; and the adapter electrode section 75 according to the present embodiment has the same configuration as that of the insertion section electrode section 32 according to the above first embodiment. Accordingly, the adapter electrode section 75 is of a fixed type, and the insertion section electrode section 74 is of a movable type as explained above.

The adapter electrode section 75 is electrically connected to the insertion section electrode section 74 upon coupling the optical adapter 12 to the insertion section 2. The opening section 35 is closed in this state.

As described above, the effect similar to that of the above first embodiment can be obtained by the endoscope apparatus 1 according to the present embodiment.

The modified examples illustrated in FIGS. 8 to 18 based on the above first embodiment are applicable to the present embodiment.

(Embodiment 3)

A third embodiment of the present invention will be next explained.

FIGS. 23 to 26 illustrate the third embodiment of the present invention.

Figure 23:
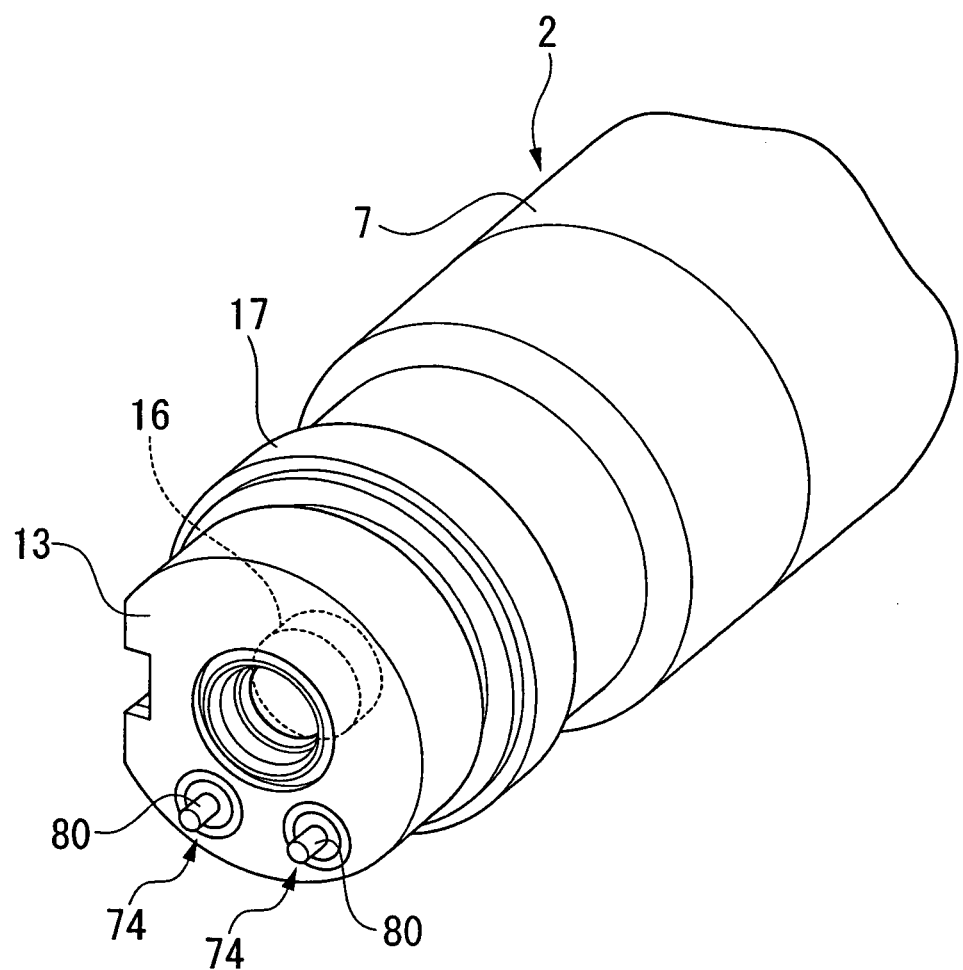
FIG. 23 shows a substantial part of the endoscopic apparatus including the tip of the insertion section according to the third embodiment of the present invention.
Figure 24:
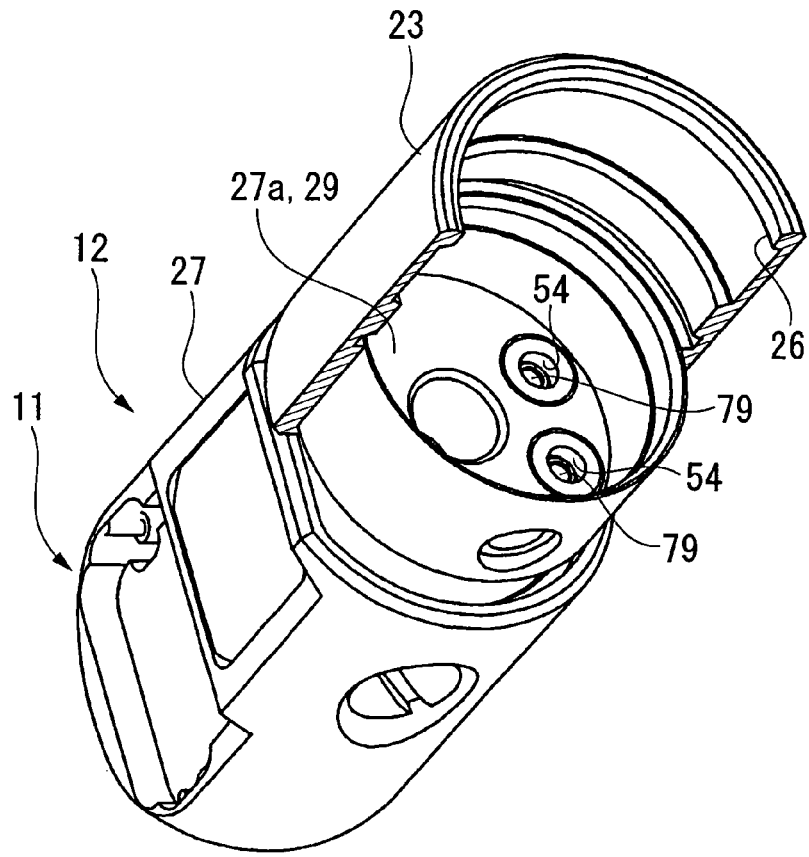
FIG. 24 shows a substantial part of the endoscopic apparatus of the third embodiment in a perspective view including a half cutaway view of the attaching hood of the optical adapter viewed from the base end.
Figure 25:
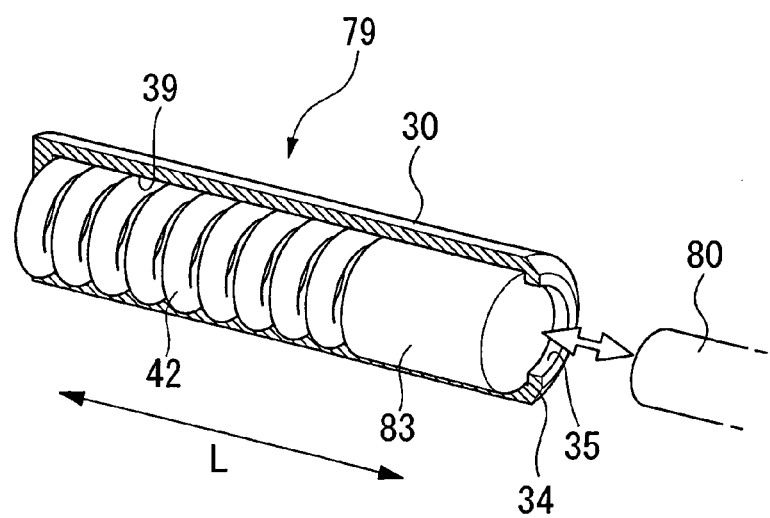
FIG. 25 illustrates the adapter electrode section of FIG. 24 in an enlarged perspective view.
Figure 26:
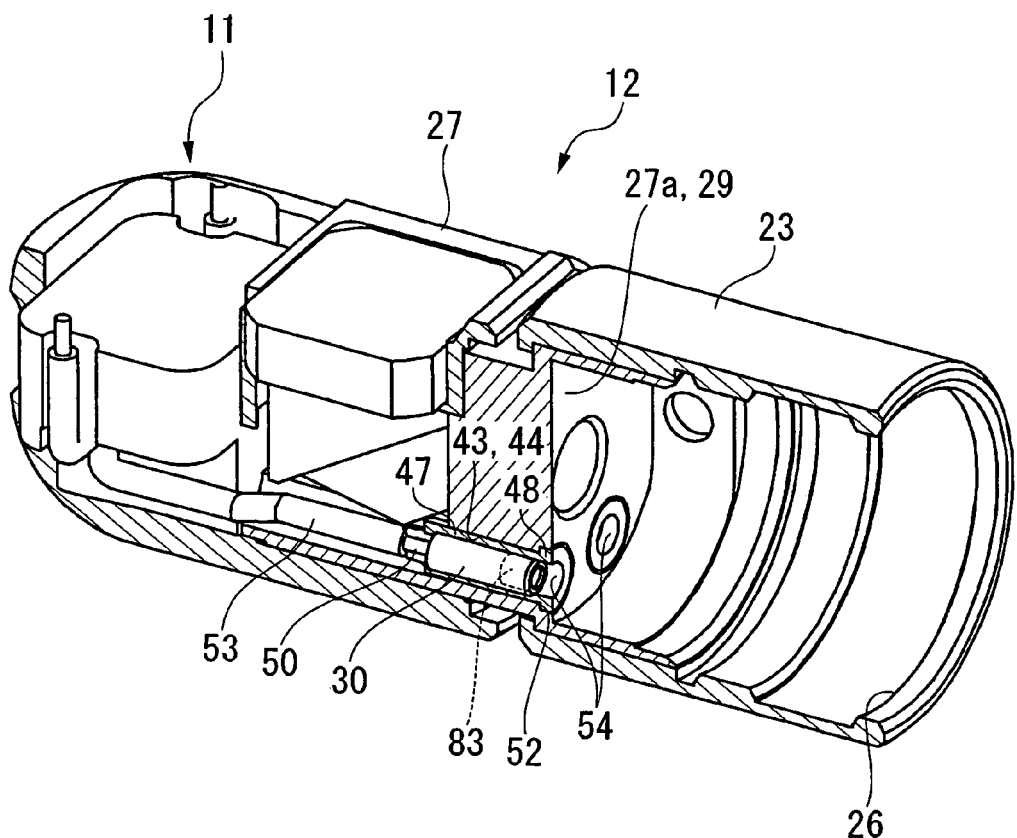
FIG. 26 is a half-cutaway view of a hollow casing shown in FIG. 24.
Figure 27:
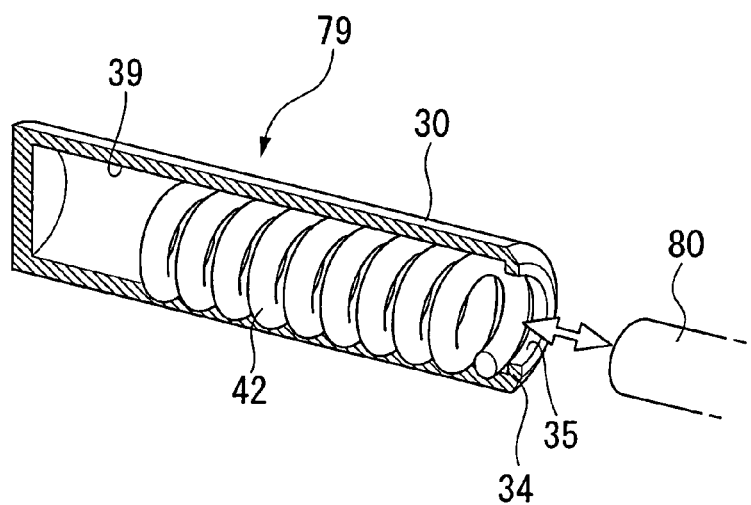
FIG. 27 illustrates a modified example of the adapter electrode section shown in FIG. 25.

As shown in FIGS. 23 and 24, an insertion section electrode section 78 is of a fixed type, and an adapter electrode section 79 is of a movable type according to the present embodiment. To be more specific, the insertion section electrode section 78 is provided with a projecting terminal (electrode terminal) 80 which is fixed on and projects from the insertion section-mounting surface 13. The adapter electrode section 79 is provided with a columnar inner-casing connection terminal 83 as illustrated in FIGS. 25 and 26 in place of the electrode terminal 31.

Also, highly conductive plating or painting is applied to the surface of the inner-casing connection terminal 83 made of metal. The inner-casing connection terminal 83 movable in the longitudinal direction L is also urged by the coil spring 42 toward the opening section 35.

The inner diameter of the opening section 35 and the outer diameter of the projecting terminals 80 are configured to be the same.

Coupling the optical adapter 12 to the insertion section 2 in this configuration inserts the projecting terminals 80 into the hollow casing 30 through the recess 54 and the opening section 35. The contact between the projecting terminals 80 and the inner-casing connection terminal 83 provides electrical connection between the adapter electrode section 79 and the insertion section electrode section 78.

As described above, the effect similar to that of the above first embodiment can be obtained by the endoscope apparatus 1 according to the present embodiment; and the rigidity of the fixed projecting terminals 80 can be significant.

The configuration of the present invention is not limited to the use of the inner-casing connection terminal 83, that is, the configuration free of the inner-casing connection terminal 83 is also practicable. In this case, the projecting terminals 80 make contact with the tip of the coil spring 42 through the opening section 35. This configuration allows the adapter electrode section 79 to be electrically connected to the insertion section electrode section 78.

In addition, it is obvious that the modified examples illustrated in FIGS. 8 to 19 based on the above first embodiment are applicable to the present embodiment.

(Embodiment 4)

A fourth embodiment of the present invention will be next explained.

Figure 28:
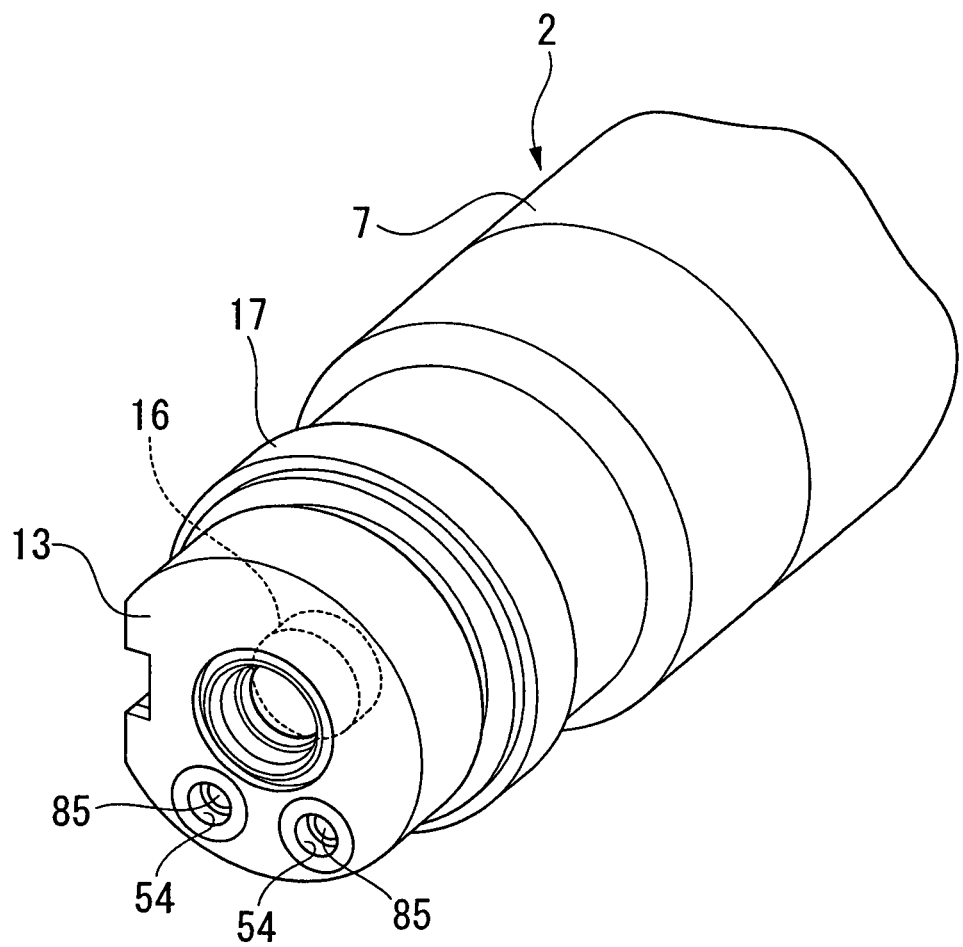
FIG. 28 shows a substantial part of the endoscopic apparatus including the tip of the insertion section according to the fourth embodiment of the present invention.
Figure 29:
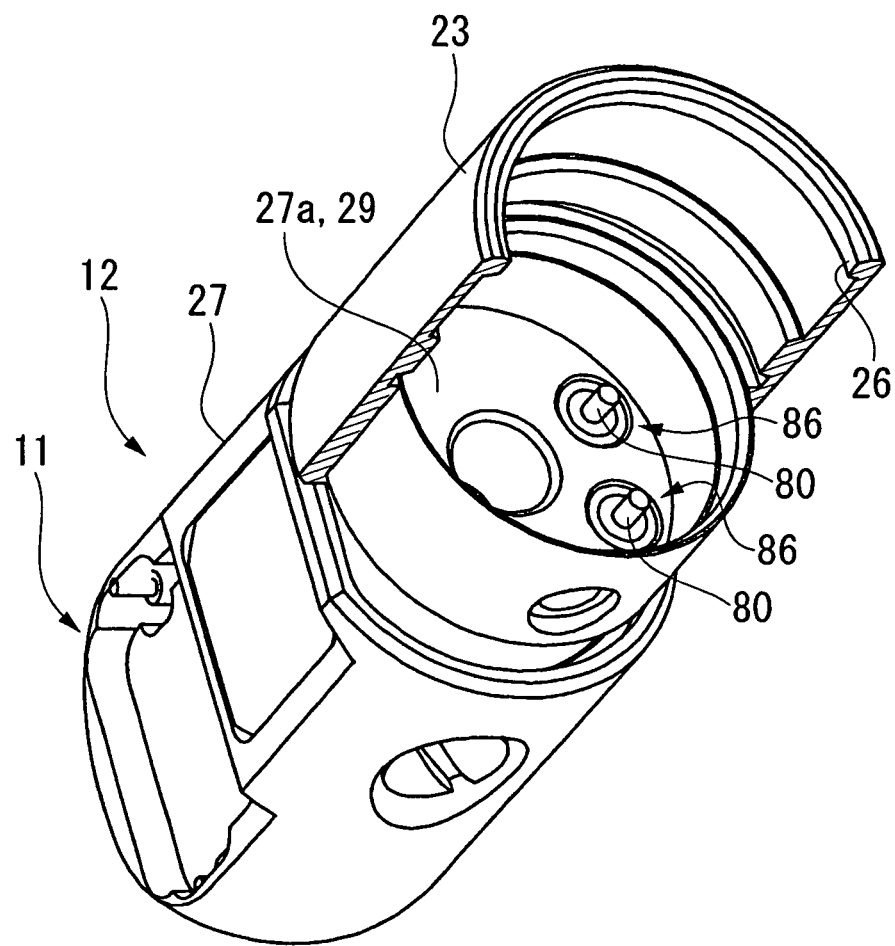
FIG. 29 shows a substantial part of the endoscopic apparatus of the fourth embodiment in a perspective view including a half cutaway view of the attaching hood of the optical adapter viewed from the base end.
Figure 30:
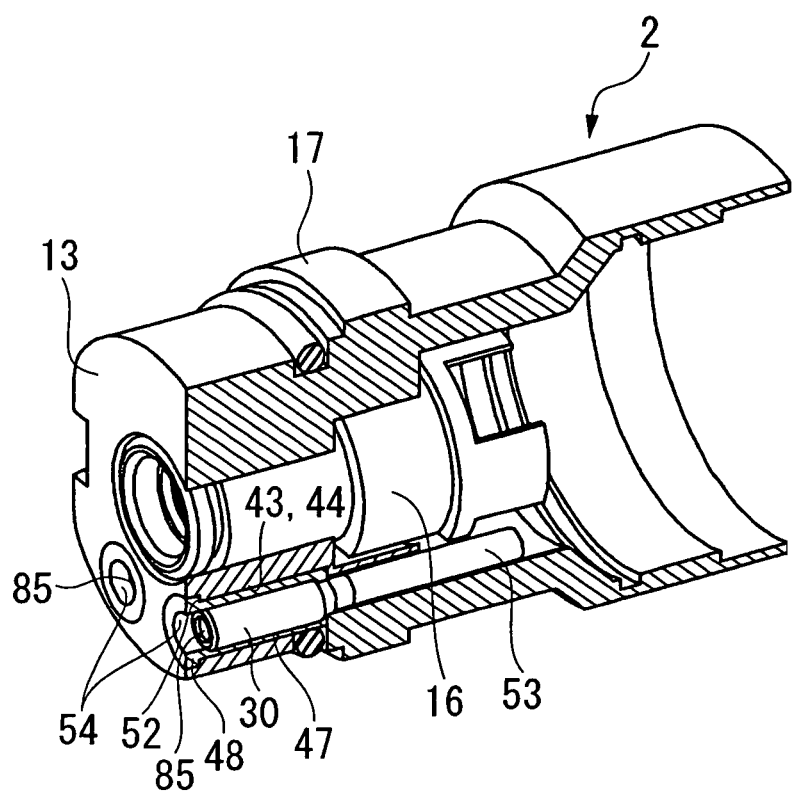
FIG. 30 is a perspective half-cutaway view of the insertion section shown in FIG. 28.

FIGS. 28 to 30 illustrate the fourth embodiment of the present invention.

The fundamental configuration of the present embodiment is the same as that of the third embodiment; only the differences will be hereafter explained.

The adapter electrode section 79 and the insertion section electrode section 78 illustrated in the third embodiment are interchangeably disposed in the endoscope apparatus 1 of the present embodiment. To be more specific, an insertion section electrode section 85 according to the present embodiment has the same configuration as that of the adapter electrode section 79 according to the above third embodiment; and the adapter electrode section 86 according to the present embodiment has the same configuration as that of the insertion section electrode section 78 according to the above third embodiment. Accordingly, the adapter electrode section 86 is of a fixed type, and the insertion section electrode section 85 is of a movable type.

The adapter electrode section 86 is electrically connected to the insertion section electrode section 85 upon coupling the optical adapter 12 to the insertion section 2. The opening section 35 is closed in this state.

As stated above, the effect similar to that of the above third embodiment can be obtained by the endoscope apparatus 1 according to the present embodiment.

In addition, it is obvious that the modified examples illustrated in FIGS. 8 to 19 based on the above first embodiment are applicable to the present embodiment.

Arbitrary modifications are practicable in the forms of the opening section 35 and other counterpart opening section 68 that are circular through the above first to fourth embodiments; and the electrode terminal 31, the other end terminal 69, and projecting terminals 80 that are columnar through the above embodiments. For example, the transverse cross section of the electrode terminal 31, etc. may be oval, and the electrode terminal 31 may be a rectangular parallelepiped.

Arbitrary modifications are also practicable to the coil spring 42, serving as an urging member, and the hollow casing 30 with respect to electrical conductivity; that is, at least one of them may have electrical conductivity.

It is understood that the adapter electrode sections 18, 75, 79, and 86 according to the present invention are not limited to be connected to the lighting section 11. These may rather be connected to other sensors and electronic components, e.g., adapter recognition sensors and temperature humidity sensors.

It is in addition understood that the present invention is not limited to the optical adapter 12 of a lateral view type having the lighting section 11 on a side wall section. The lighting section 11 may rather be of a direct view type provided onto the tip of the optical adapter 12.

The present invention is not limited to the first to fourth embodiments, and various modifications may be made without departing from the spirit of the present invention.

For example, the first to fourth embodiments above having disclosed the electrodes disposed to one of the adapter and the insertion section may include the configuration of one electrode to the adapter and the other one to the insertion section. The adapter and the insertion section may each have two electrodes in another configuration. This configuration advantageously maintains an adapter and an insertion section to be small in outside shape.

(Embodiment 5)

An endoscopic apparatus according to a fifth embodiment of the present invention will be explained with reference to the attached drawings.

FIG. 1 illustrates the endoscope device according to the fifth embodiment of the present invention.

The endoscope apparatus 1 is provided with an insertion section 2 (endoscopic insertion section) having a bending section 7 capable of bending; and a main body section 3 (endoscope main body section) variously operable when used with the insertion section 2 inserted thereinto.

The approximately box-shaped main body section 3 has a side wall section onto which an operation panel 6 is disposed used for carrying out various operations. In addition, a monitor 8 for exhibiting an observed image is disposed on a ceiling of the main body section 3. Furthermore, a power supply section 9 for supplying electric power is disposed to the main body section 3.

Figure 31:
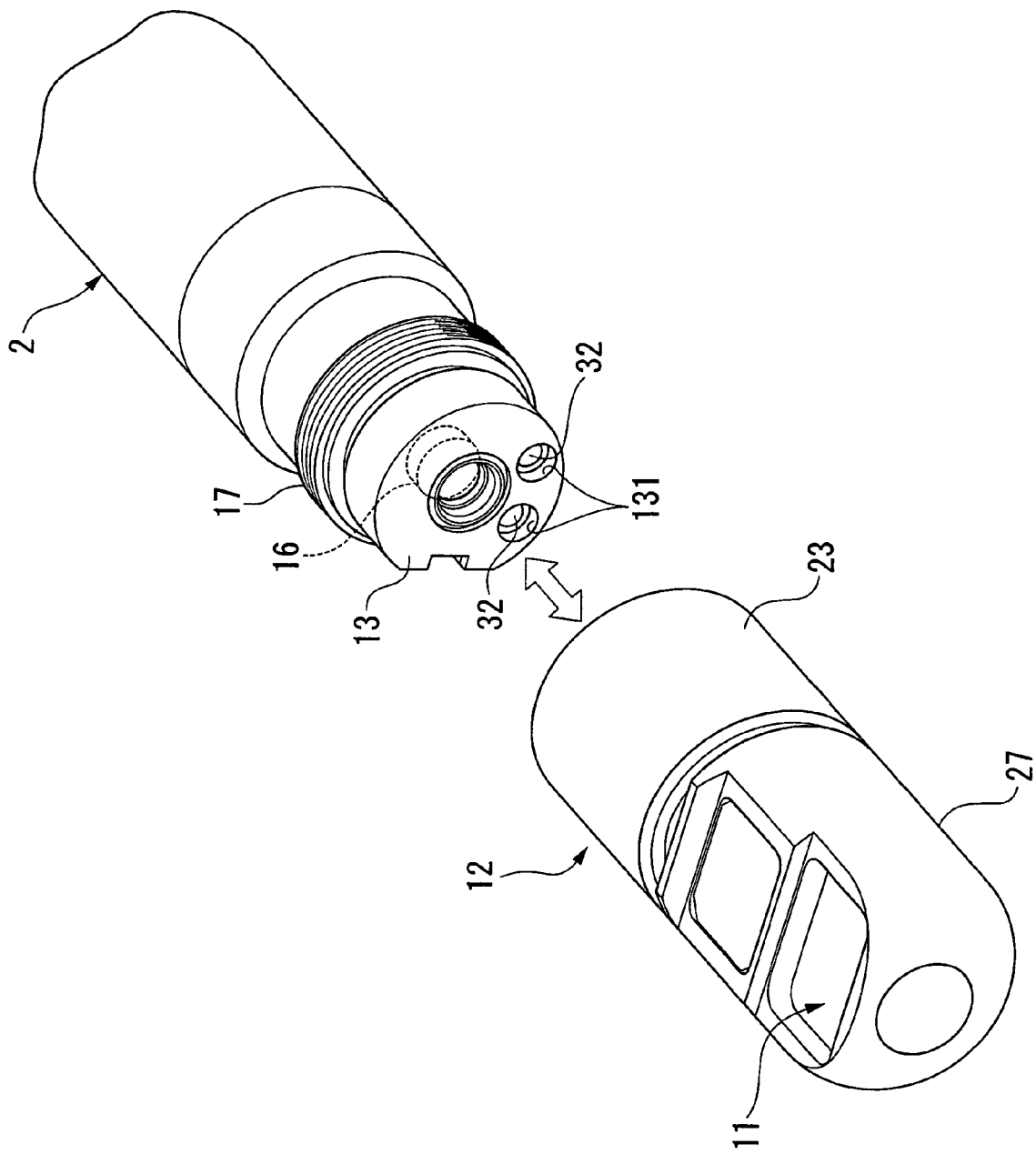
FIG. 31 illustrates the insertion section of the endoscopic apparatus shown in FIG. 1 including the attaching surface to which the optical adapter is detachably attached.

Also, the base end section of the insertion section 2 is configured to be detachably attached to the main body section 3 through a connecting section which is not shown in the drawings. Meanwhile an observing unit using a CCD 16 is disposed onto the tip thereof as shown in FIG. 31. In addition, a fitting-protrusion section 17 is disposed extending over the circumference of the insertion section 2. An insertion section-mounting surface 13 is disposed on the tip of the insertion section 2 so that an optical adapter (adapter) 12 having an object lens which is not shown in the drawing is detachably attached onto the surface 13.

Figure 32:
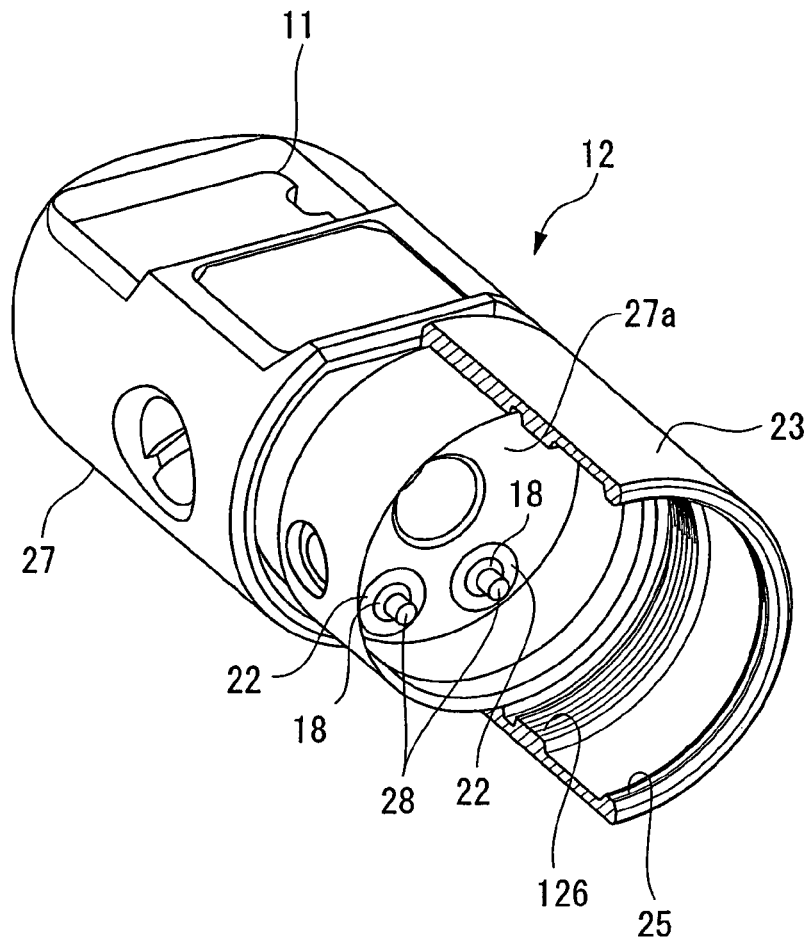
FIG. 32 is an enlarged view of the optical adapter shown in FIG. 1 viewed from the base end including an attaching hood approximately half of which is illustrated in a cutout view.

The optical adapter 12 is provided with an approximately columnar adapter main body 27 and an approximately cylindrical attachment hood section 23 as shown in FIG. 32. The adapter main body 27 is coaxially and rotatably coupled to the attachment hood section 23.

Figure 33:
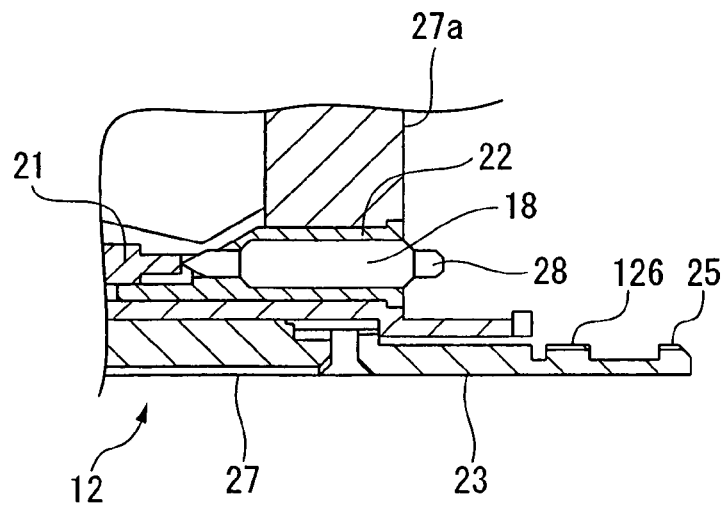
FIG. 33 illustrates the substantial peripheral part of the adapter electrode section shown in FIG. 32 in a cross sectional view.

Provided onto the side wall section of the adapter main body 27 is a lighting section 11 having, for example, LEDs. Provided on a bottom surface section 27a of the adapter main body 27 is an adapter electrode section 18 connected to the lighting section 11 through a cable 21 shown in FIG. 33. Highly conductive plating or painting is applied to the surface of the adapter electrode section 18 made of nonferrous metals or ferrous metals, e.g., iron. The adapter electrode section 18 is also provided with protrusion electrode sections 28 projecting from the bottom surface section 27a outward in the longitudinal direction of the optical adapter 12. Provided around the adapter electrode section 18 is an insulative member 22.

A first female thread section 25 and a second female screw section 126 are cut fully on the inner periphery of the attachment hood section 23 so that a predetermined interval is disposed between the screw sections.

Inserting the tip of the insertion section 2 from the rear end of the optical adapter 12 and rotating the attachment hood section 23 screw first the male thread section 17 into the first female thread section 25. Rotating further the attachment hood section 23 screws the male thread section 17 into the second female screw section 126 across the first female thread section 25, thereby causing the optical adapter 12 to be detachably coupled to the mounting surface 13. That is, the first female thread section 25 works as a retainer restraining the optical adapter 12 from removing from the insertion section 2.

Figure 34:
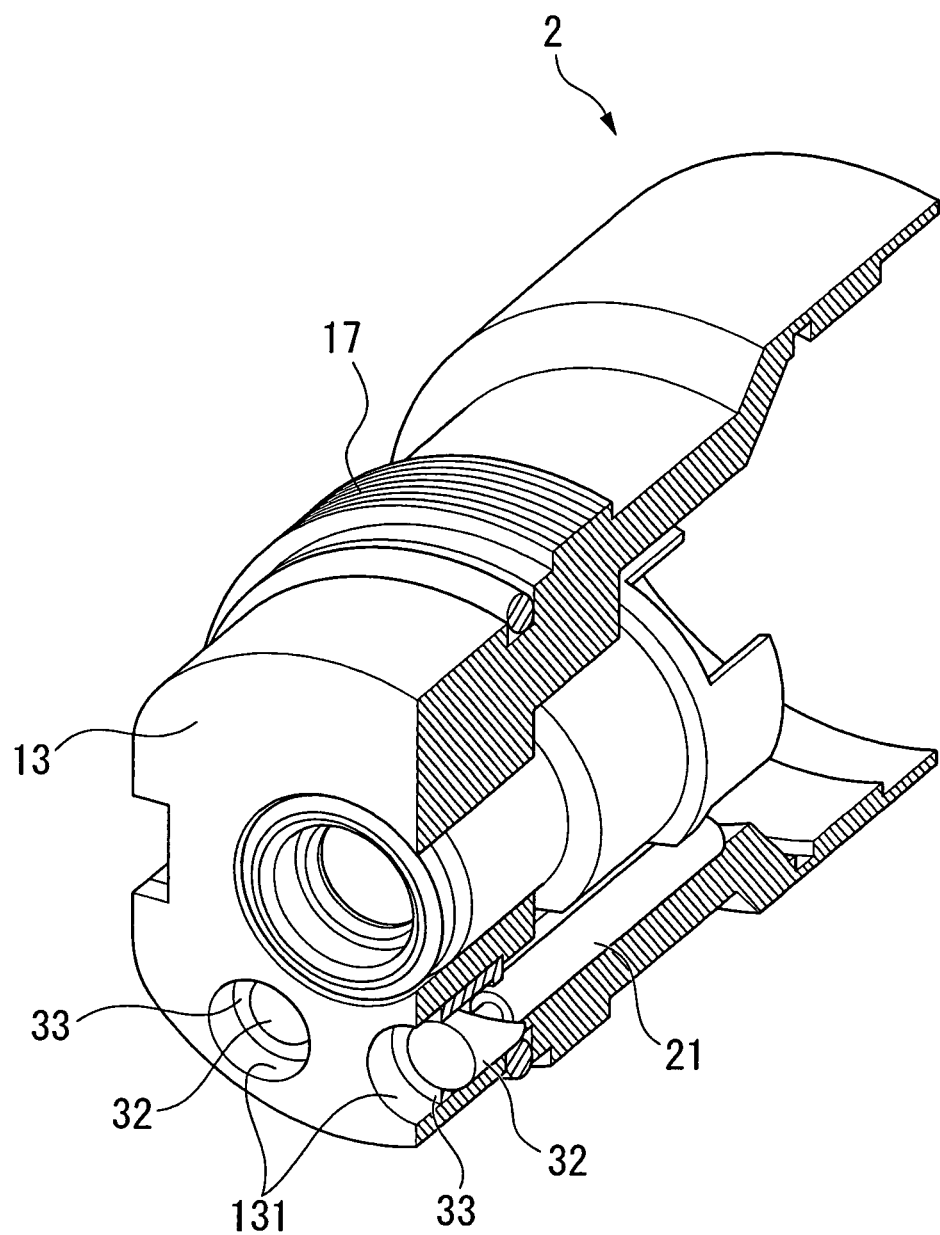
FIG. 34 is an enlarged half cutaway view of the tip of the insertion section viewed from the tip.
Figure 35:
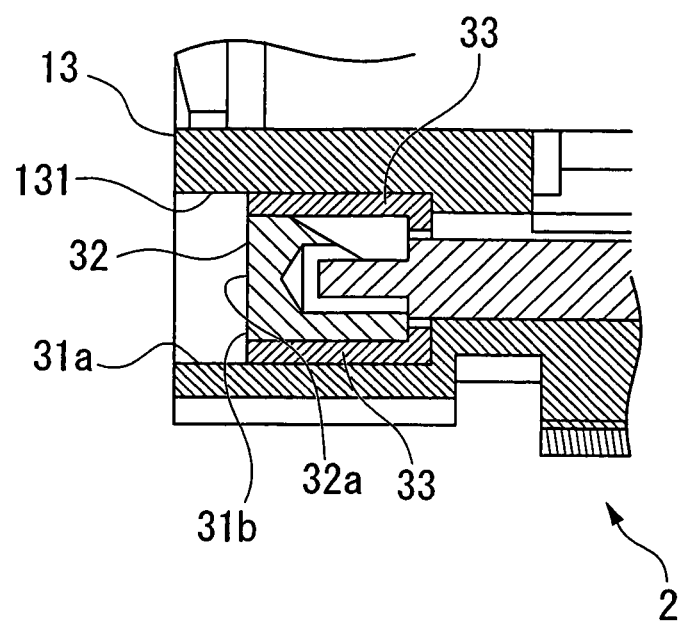
FIG. 35 illustrates the substantial peripheral part of the insertion electrode section shown in FIG. 34 in a cross sectional view.

Provided on the mounting surface 13 of the insertion section 2 in the present embodiment as shown in FIG. 34 are two recesses 131 each accommodating thereinside an insertion section electrode section 32 having a bottom section and a cylinder section. To be more specific, in a recess 131 formed by a side wall section 31a and a bottom surface section 31b as shown in FIG. 35, an end surface section 32a of the insertion section electrode section 32 is disposed to be flush with the bottom surface section 31b. The insertion section electrode section 32 is therefore disposed recessed relative to the mounting surface 13 toward the insertion section 2.

Also, highly conductive plating or painting is applied to the surface of the insertion section electrode section 32 made of nonferrous metals or ferrous metals, e.g., iron. The insertion section electrode section 32 is further connected to the power supply section 9 as shown in FIG. 1 through the cable 21. Attaching then the optical adapter 12 to the mounting surface 13 provides contact between the protrusion electrode section 28 and the end surface section 32a of the insertion section electrode section 32, thereby providing electrical connection between the adapter electrode section 18 and the insertion section electrode section 32 and thus supplying electrical power from the power supply section 9 to the lighting section 11. Provided around the insertion section electrode section 32 is an insulative member 33.

The operation of the endoscope apparatus 1 thus configured in the present embodiment will be explained next.

A selected one of desirable optical adapter 12 is attached first to the mounting surface 13 of the insertion section 2 as explained previously. This electrically connects the adapter electrode section 18 to the insertion section electrode section 32, thereby supplying electric power to the lighting section 11 from the power supply section 9. The lighting section 11 of the insertion section 2 introduced into a object subject to inspection emits light. The light reflected by the object subject to inspection passes through object lenses in the optical adapter 12 and an image thereof is formed on a CCD 16.

A signal output from the CCD 16 is supplied to a monitor 8 through a predetermined circuit. This provides an observed image exhibited on the monitor 8 used for a predetermined inspection of the object. The optical adapter 12 attached to the mounting surface 13 is detached and replaced by another optical adapter 12 required for inspecting another object. Another selected one of the optical adapter 12 is then attached to the mounting surface 13. This is how the optical adapters 12 are exchanged.

The insertion section electrode section 32 accommodated in the recess 131 is surrounded by the side wall section 31a forming the recess 131 while the optical adapter 12 is in the detached state in the present embodiment. This conceals the insertion section electrode section 32 behind the mounting surface 13.

As described above, the endoscope apparatus 1 according to the present embodiment advantageously prevents the appearance of the insertion section electrode section 32 from the mounting surface 13 with the optical adapter 12 detached. Accordingly, the insertion section electrode section 32 can be protected from short circuit, failure, and dust entry, thereby maintaining the insertion section electrode section 32 clean with the optical adapter 12 detached from the insertion section 2.

The insertion section electrode section 32 having the bottom section, the cylinder section, and the end surface section 32a directed outward is effectively protected from dust entry.

Also, coupling the optical adapter 12 to the mounting surface 13 connects the end surface section 32a of the insertion section electrode section 32 to the tip of the protrusion electrode section 28, thereby providing an interfacial contact between the insertion section electrode section 32 and the adapter electrode section 18. The electrical conductivity between the insertion section electrode section 32 and the adapter electrode section 18 can be obtained in the case of lower component quality or lower assembly accuracy.

The highly conductive plating or painting provided onto the insertion section electrode section 32 and the adapter electrode section 18 lowers the electrical loss between the insertion section electrode section 32 and the adapter electrode section 18.

Incidentally, the present embodiment is not limited to the configuration disclosing the protrusion electrode section 28 fixed to the adapter electrode section 18 and the end surface section 32a fixed to the insertion section electrode section 32, i.e., at least one of them may be movable.

Figure 36:
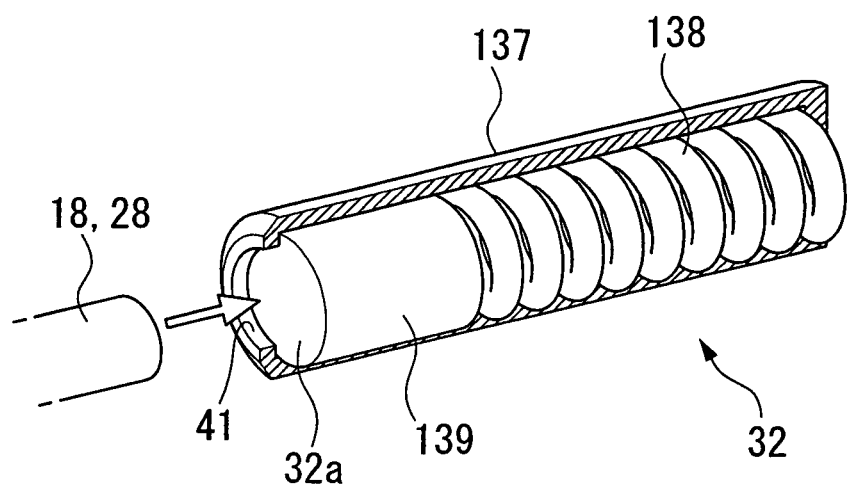
FIG. 36 illustrates a modified example of the insertion section electrode shown in FIG. 34 in a perspective view including a half cutaway view of a cylindrical main body.
Figure 37:
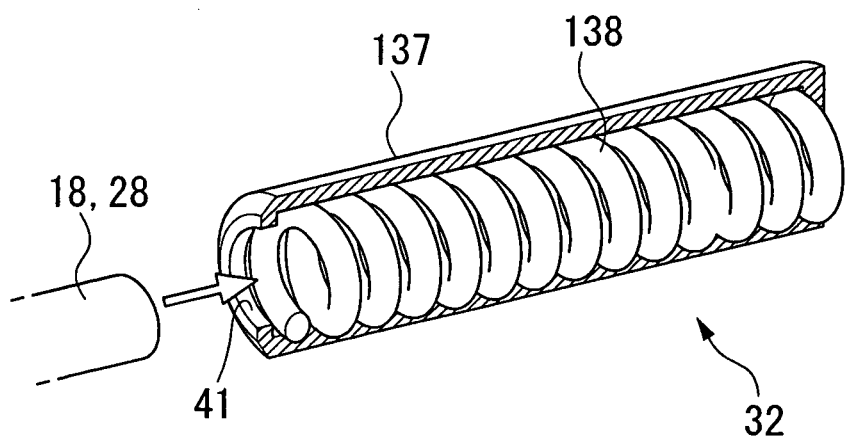
FIG. 37 illustrates another modified example of the insertion section electrode shown in FIG. 34 in a perspective view including a half cutaway view of the cylindrical main body.

For example, the insertion section electrode section 32 as shown in FIG. 36 may comprise a main body cylinder section 137 having a bottom section and a cylinder section; a spring 138 disposed in the main body cylinder section 137; and a columnar electrode terminal section 139 disposed to the tip of the spring 138 so as to be movable in the longitudinal direction of the main body cylinder section 137. The tip of the main body cylinder section 137 is then disposed at the bottom surface section 31b forming the recess 131.

Coupling the optical adapter 12 to the mounting surface 13 in this configuration inserts the protrusion electrode section 28 into the main body cylinder section 137 through the opening 41 disposed at the tip of the main body cylinder section 137. The electrode terminal section 139 moves accordingly while resisting the thrust force exerted by the spring 138. This facilitates the connection between the protrusion electrode section 28 and the end surface section 32a, and the resilience of the spring 138 absorbs manufacturing error in the adapter electrode section 18 and the insertion section electrode section 32, etc. Equalizing the outer diameter of the protrusion electrode section 28 to the inner diameter of the opening 41 provides the constant blockage of the interspace between the protrusion electrode section 28 and the opening 41 irrespective of the position of the protrusion electrode section 28 inserted into the insertion section electrode section 32, thereby more effectively preventing dust entry.

Also, another configuration having only a spring 138 in the main body cylinder section 137, i.e., without the electrode terminal section 139 may be practicable. Coupling the optical adapter 12 to the mounting surface 13 in this configuration inserts the protrusion electrode section 28 into the main body cylinder section 137 through the opening 41 disposed at the tip of the main body cylinder section 137. The spring 138 contacting the tip of the protrusion electrode section 28 is then thrusted. This simple configuration facilitates the electrical connection between the protrusion electrode section 28 and the spring 138.

The number of the recesses 131 and insertion section electrode sections 32 disposed in the present embodiment may be modified arbitrarily irrespective of the previously described disposition in which one recess 131 has one insertion section electrode section 32.

For example, three or more insertion section electrode sections 32 may practicably be disposed.

Figure 38:
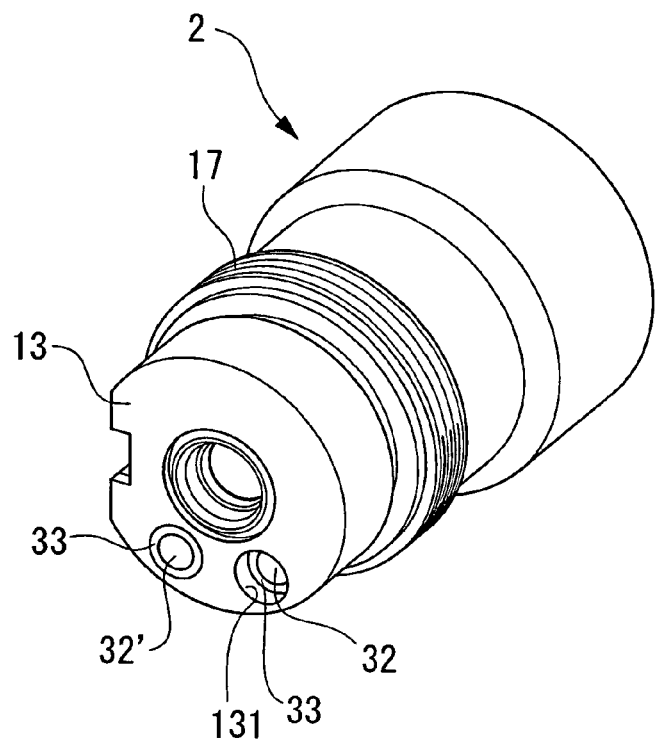
FIG. 38 illustrates modified examples of a recess and the insertion section electrode that are shown in FIG. 31.
Figure 39:
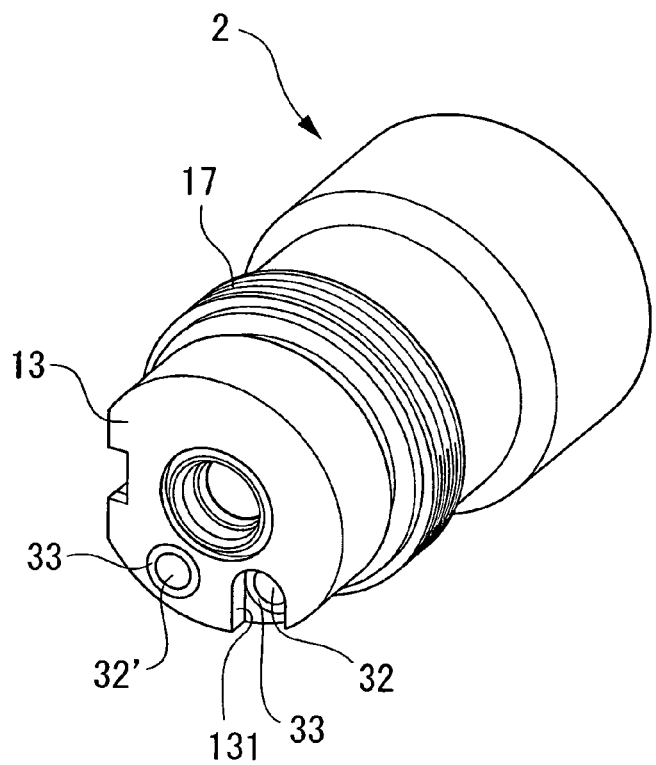
FIG. 39 illustrates modified examples of the recess and the insertion section electrode that are shown in FIG. 31 and a notch section formed on the recess shown in FIG. 38.

FIG. 38 illustrates an example in which a recess 131 disposed on the mounting surface 13 has an insertion section electrode section 32, and an insertion section electrode 32' is disposed on a portion of the mounting surface 13 except the recess 131.

Figure 41:
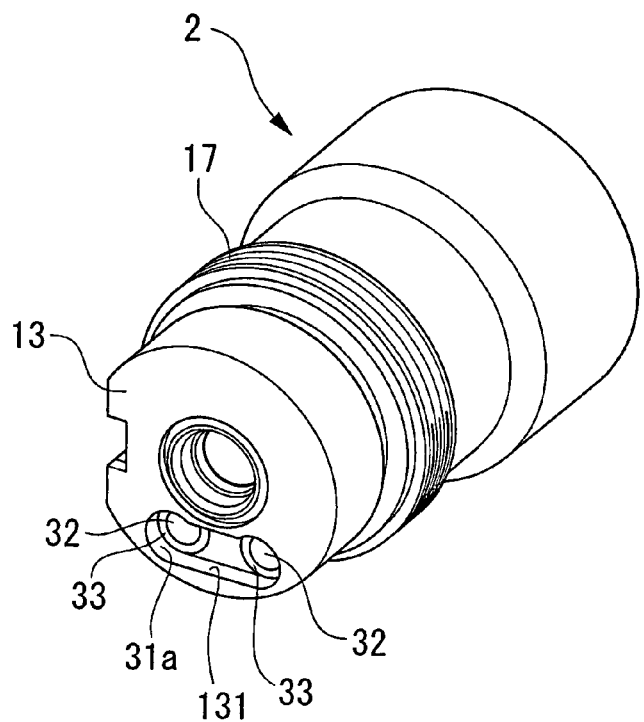
FIG. 41 illustrates modified examples of FIG. 31 having a recess having a plurality of insertion section electrodes.

Furthermore, FIG. 41 practically shows an example in which two insertion section electrodes 32a are disposed in a recess 131. The simple and low cost configuration that can be shortly obtained facilitates cleaning inside the recess 131. The number of insertion section electrode sections 32 disposed in the recess 131 in this case may not be limited to two, i.e., it can be arbitrarily modified. That is, a plurality of insertion section electrode sections 32 may be disposed in one common recess 131 formed on the mounting surface 13; and some of the insertion section electrode sections 32 may be separately disposed at a plurality of recesses 131. Alternatively, some of the insertion section electrode sections 32 may be disposed in the recess 131.

Figure 40:
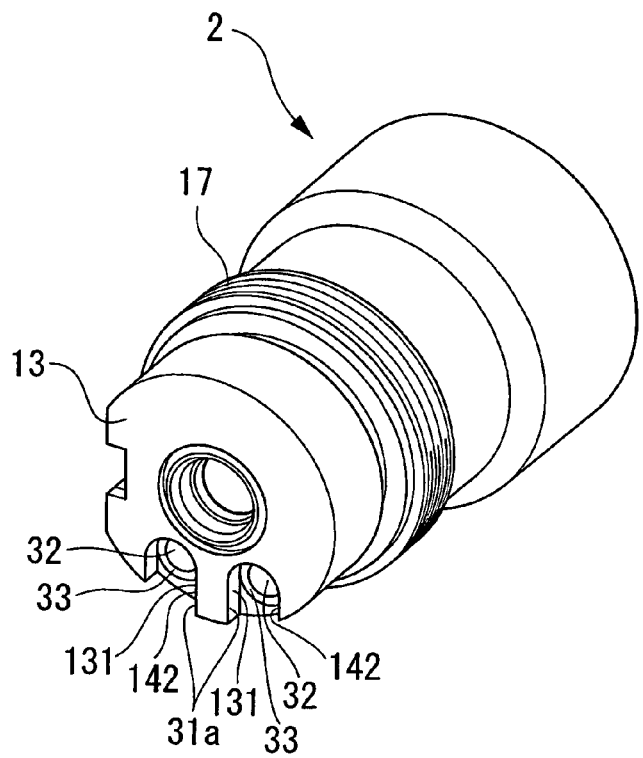
FIG. 40 illustrates modified examples of two recesses and the insertion section electrode that are shown in FIG. 31 and a notch section formed on each recess shown in FIG. 31.

Also, FIG. 40 practicably shows an example in which two recesses 131 each has a notch section 142.

Furthermore, FIG. 41 practicably shows an example in which two insertion section electrodes 32a are disposed in a recess 131. The simple and low cost configuration that can be shortly obtained facilitates cleaning inside the recess 131. The number of insertion section electrodes 32 disposed in the recess 131 in this case may not be limited to two, i.e., it can be arbitrarily modified. That is, a plurality of insertion section electrodes 32 may be disposed in one common recess 131 formed on the mounting surface 13; and some of the insertion section electrodes 32 may be separately disposed at a plurality of recesses 131. Alternatively, some of the insertion section electrodes 32 may be disposed in the recess 131.

Figure 42:
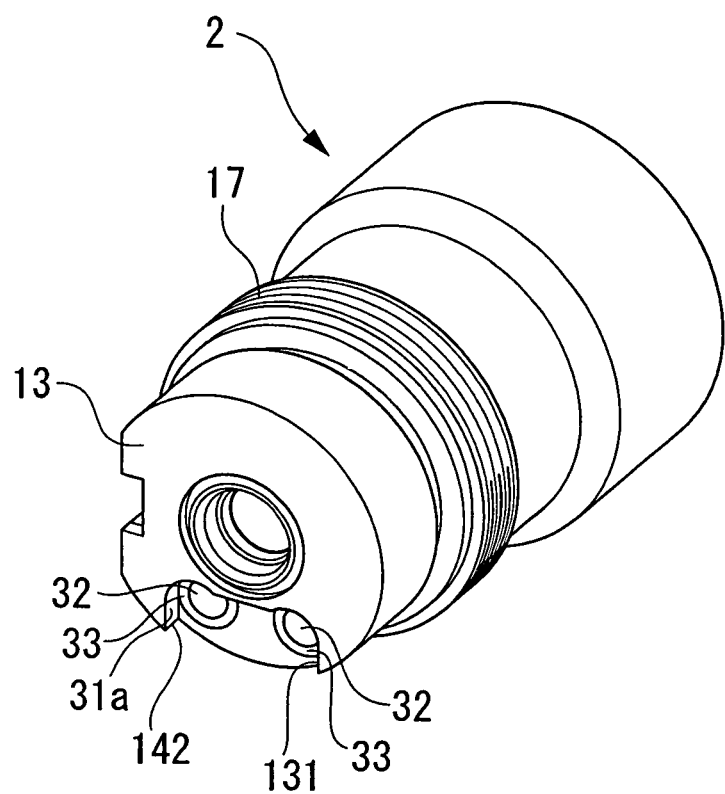
FIG. 42 illustrates modified examples of the recess and the insertion section electrodes that are shown in FIG. 31 and a notch section formed on the recess shown in FIG. 41.

Also, FIG. 42 practicably shows an example in which the recess 131 accommodates a plurality of insertion section electrode sections 32 and has a notch section 142.

(Embodiment 6)

A sixth embodiment of the present invention will be next explained.

FIGS. 33 to 44 illustrate the sixth embodiment of the present invention.

Figure 43:
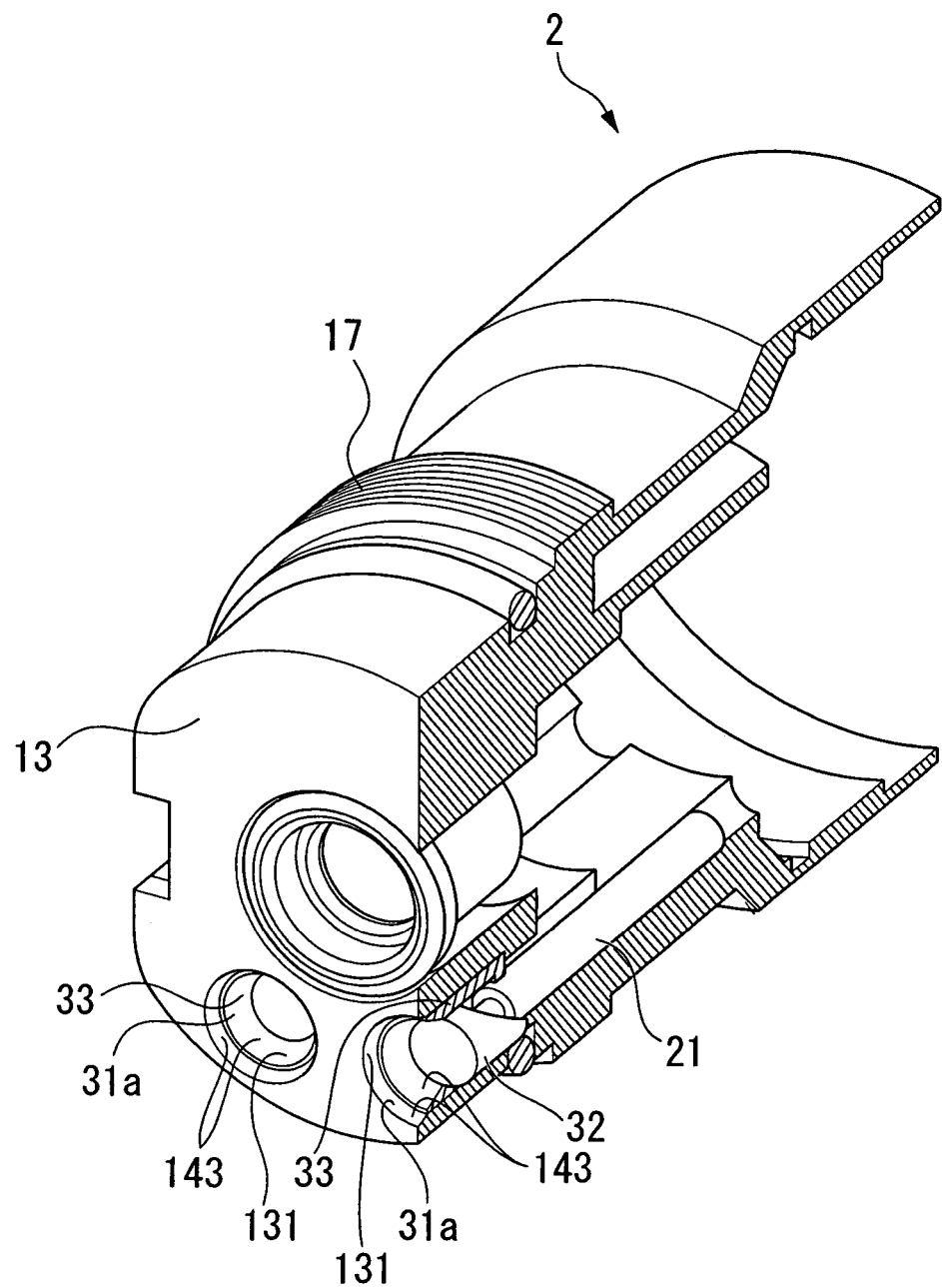
FIG. 43 shows a substantial part of the endoscopic apparatus including a half cutaway view of the tip of the insertion section according to the sixth embodiment of the present invention.
Figure 44:
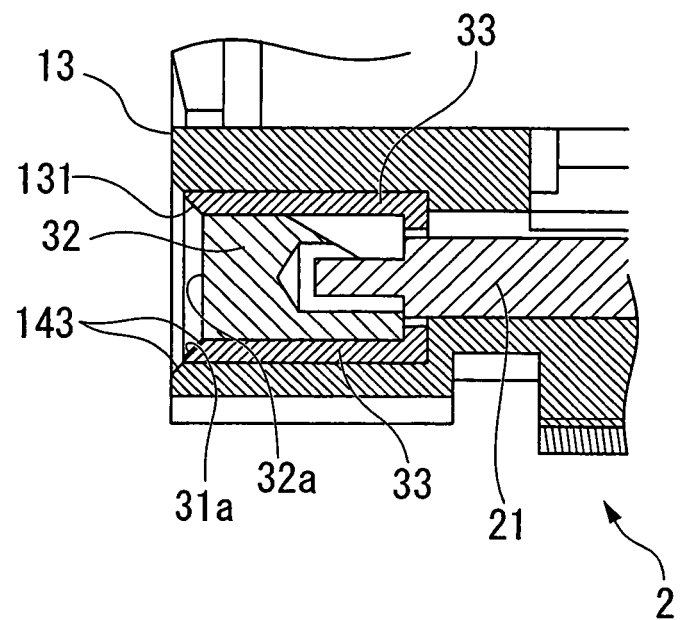
FIG. 44 illustrates the substantial peripheral part of the insertion electrode section shown in FIG. 43 in a cross sectional view.

The same reference numerals are added to the elements illustrated in FIGS. 43 and 44 that are the same as those illustrated in FIGS. 1 to 31 so as to omit duplicate explanation.

The fundamental configuration of the present embodiment is the same as that of the fifth embodiment; only the differences will be hereafter explained.

A side wall section 31a of the recess 131 is configured to incline so as to gradually expand in a radial direction outward relative to the recess 131. In other words, the side wall section 31a is a tapered section (recess section's tapered section) 143. The inclination of the tapered section 143 prevents dusts from entering the recess 131 and sticking thereto.

The configuration described above prevents dusts from clogging in the vicinity of the insertion section electrode section 32, thereby improving the workability in cleaning inside the recess 131.

(Embodiment 7)

A seventh embodiment of the present invention will be next explained.

Figure 45:
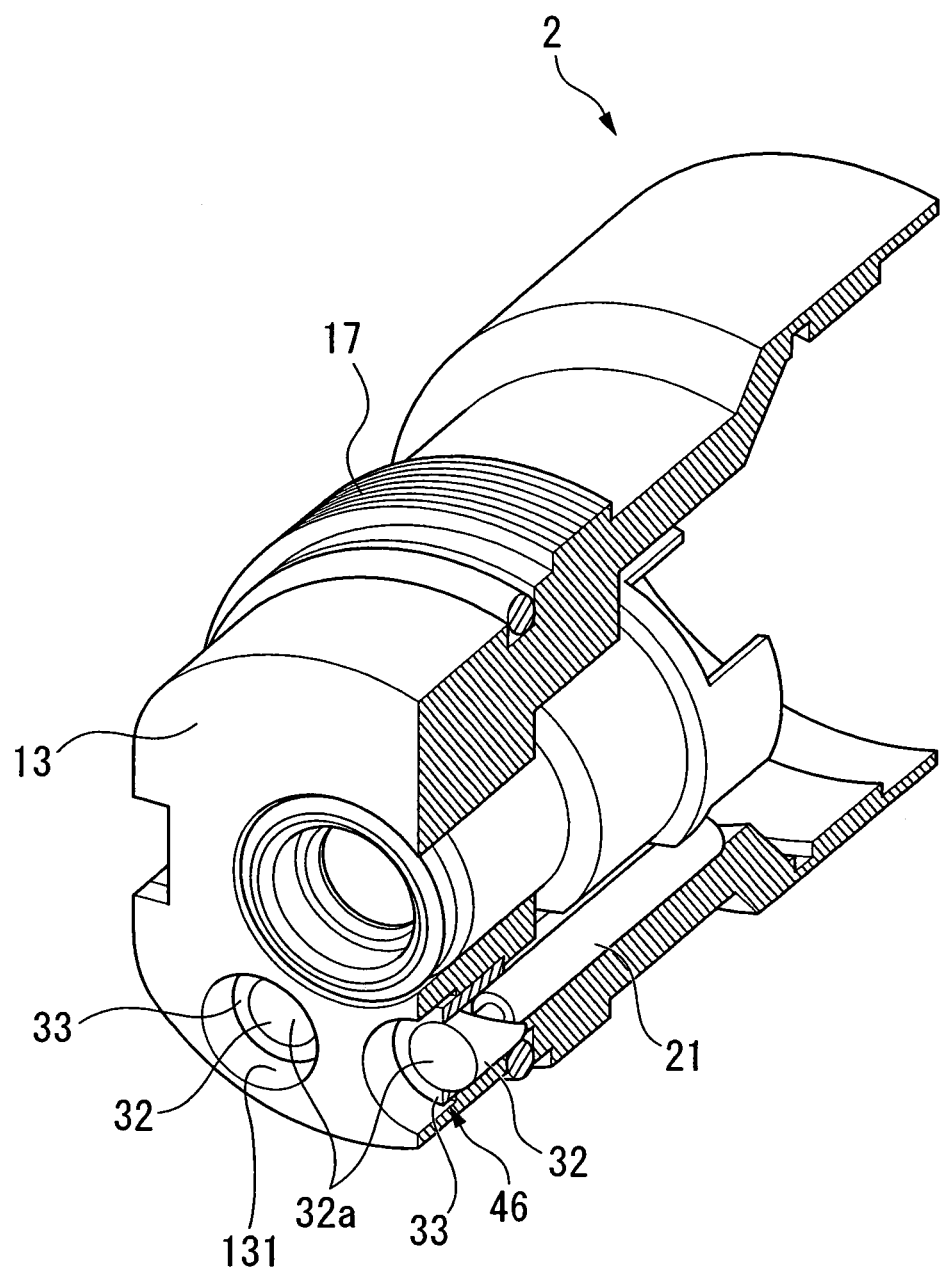
FIG. 45 shows a substantial part of the endoscopic apparatus including a half cutaway view of the tip of the insertion section according to the seventh embodiment of the present invention.
Figure 46:
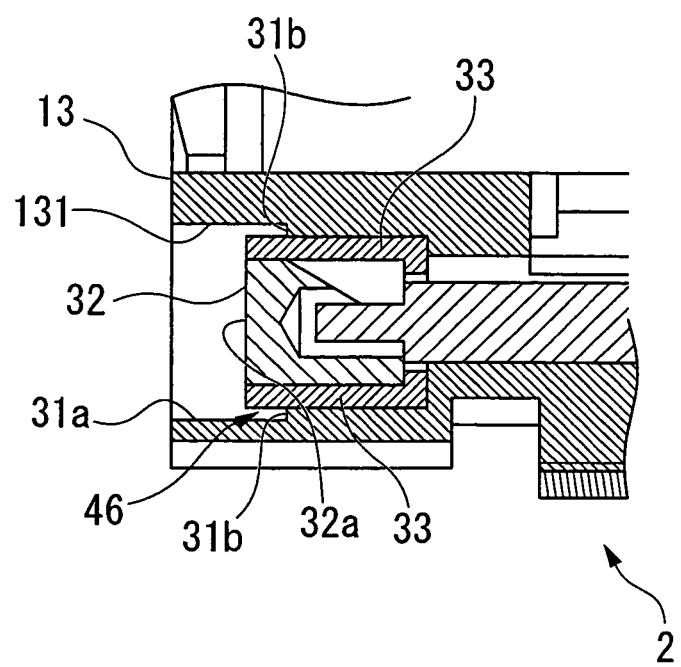
FIG. 46 illustrates the substantial peripheral part of the insertion electrode section shown in FIG. 45 in a cross sectional view.

FIGS. 45 and 46 illustrate the seventh embodiment of the present invention.

An end surface section 32a of the insertion section electrode section 32 projects more frontward relative to a bottom surface section 31b of the recess 131 in the present embodiment. That is, a groove (groove in a recess) 46 extends around and in the vicinity of the circumference of the insertion section electrode section 32.

If dust has entered the recess 131, it would access the groove 46 in this configuration. Therefore, dust accumulates in the groove 46 instead of clogging in the insertion section electrode section 32.

As described above, poor electrical contact due to dust accumulating on the insertion section electrode section 32 can be prevented.

The present invention is not limited to the configuration in which the groove 46 extending over the circumference of the insertion section electrode section 32 is disposed, that is, the groove 46 may be arbitrarily modified with respect to its size and position.

Figure 47:
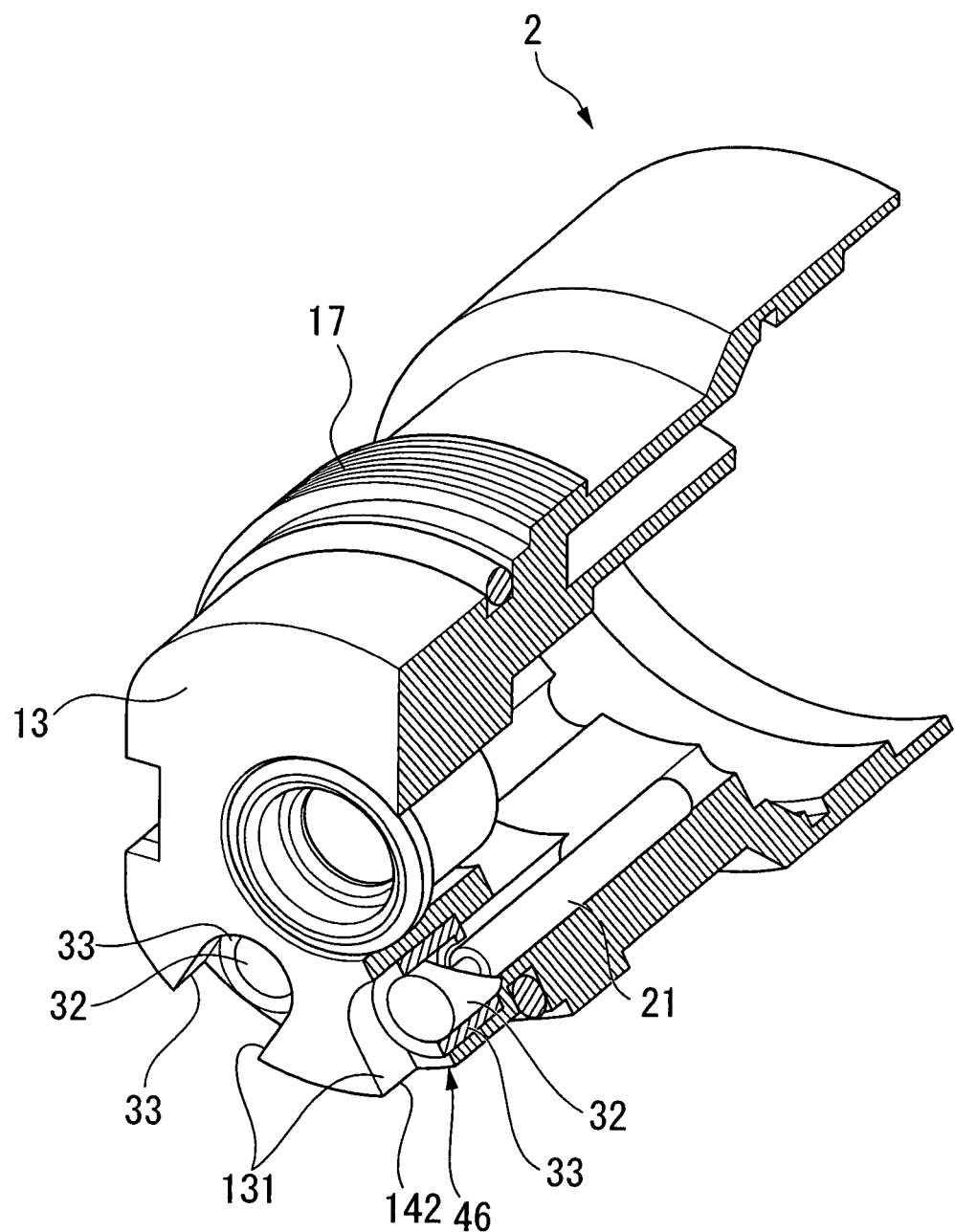
FIG. 47 illustrates a modified example of a groove shown in FIG. 45 in a perspective view including a half cutaway view of the tip of the insertion section.
Figure 48:
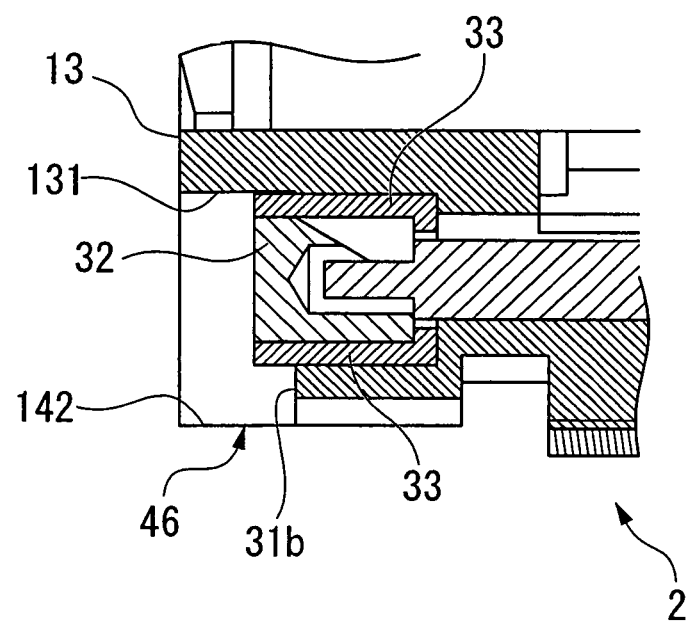
FIG. 48 illustrates the substantial peripheral part of the insertion electrode section shown in FIG. 47 in a cross sectional view.

FIGS. 47 and 48 show an example in which a groove 46 is disposed along the length of the notch section.

(Embodiment 8)

An eighth embodiment of the present invention will be next explained.

Figure 49:
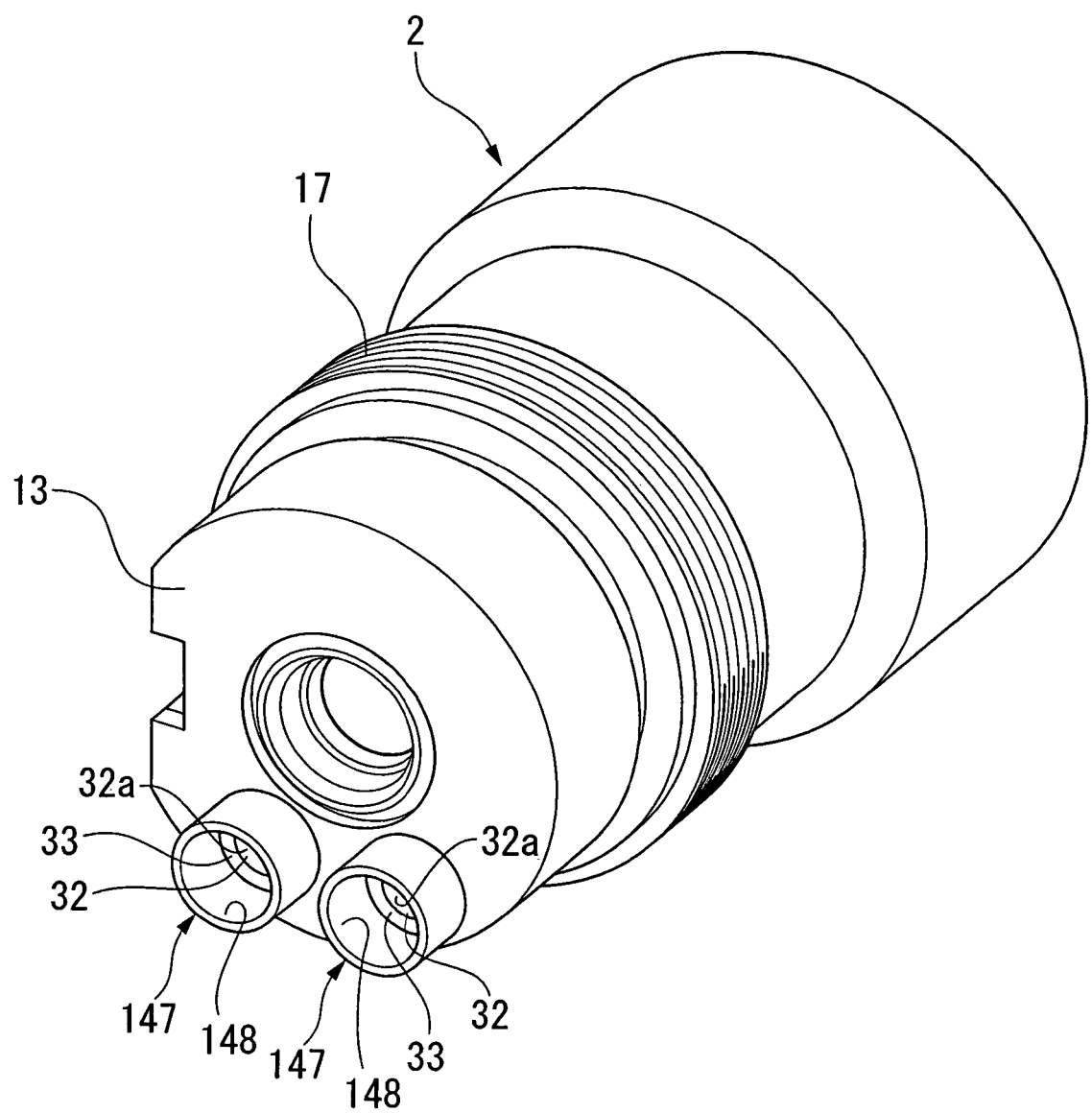
FIG. 49 illustrates substantial parts of the eighth embodiment of the endoscopic apparatus according to the present invention in a perspective view.
Figure 50:
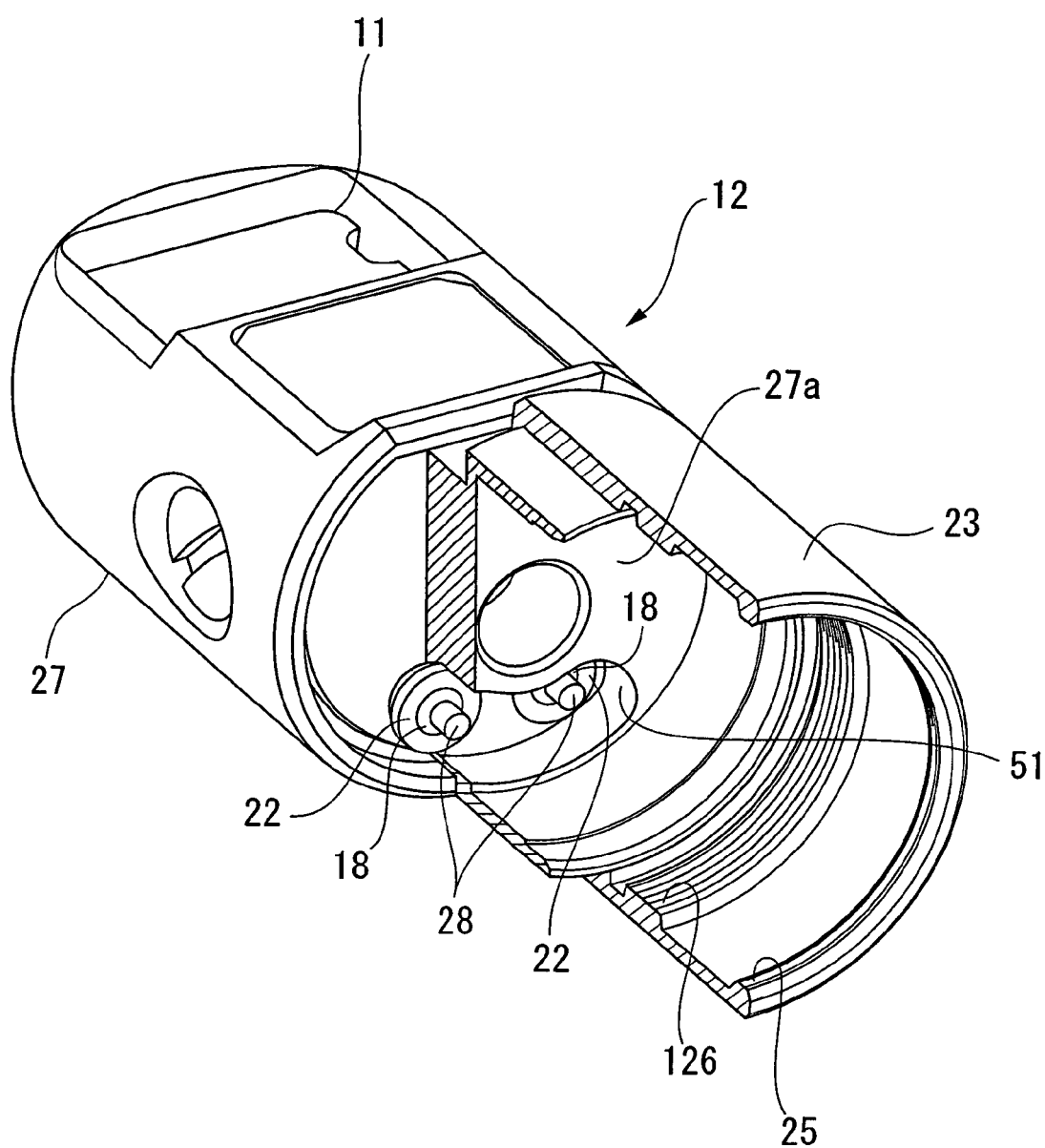
FIG. 50 illustrates the optical adapter viewed from the base end according to an embodiment including a half cutaway view of the base end section.

FIGS. 49 and 50 illustrate the eighth embodiment of the present invention.

Provided onto the mounting surface 13 according to the present embodiment shown in FIG. 49 are projecting sections 147 projecting from the mounting surface 13 along an axial line of the insertion section 2. The projecting sections 147 are cylindrical in shape. To be more specific, provided in the center of the projecting sections 147 is a hollow section 148 projecting in the same direction as that of the projecting sections 147. Provided in the hollow section 148 is an insertion section electrode section 32. The end surface section 32a of the insertion section electrode section 32 is configured to be flush with the mounting surface 13, thus the insertion section electrode section 32 is located more frontward, i.e., closer to the mounting surface 13 relative to the tip of the projecting sections 147.

As shown in FIG. 50, provided on the bottom surface section 27a of the optical adapter 12 is an adapter-recessing section 51 accommodating a protrusion electrode section 28.

Coupling the optical adapter 12 to the mounting surface 13 in this configuration disposes the projecting sections 147 into the adapter-recessing section 51, thereby contacting the protrusion electrode section 28 to the end surface section 32a of the insertion section electrode section 32 through the hollow section 148. This configuration allows the adapter electrode section 18 to be electrically connected to the insertion section electrode section 32. Since the insertion section electrode section 32 accommodated in the hollow section 148 is surrounded by the projecting sections 147, and the insertion section electrode section 32 is disposed closer to the mounting surface 13 relative to the tip of the projecting sections 147, this conceals the insertion section electrode 32 behind the mounting surface 13.

As described above, the endoscope apparatus 1 according to the present embodiment advantageously prevents the appearance of the insertion section electrode section 32 from the mounting surface 13 with the optical adapter 12 detached. The present embodiment can exhibit substantially the same effect as that of the previously described fifth embodiment.

The number of adapter-recessing sections 51 in the present embodiment may be modified arbitrarily irrespective of one piece of the adapter-recessing section 51 previously described.

The number of projecting sections 147 and insertion section electrode sections 32 disposed in the present embodiment may be modified arbitrarily irrespective of the previously described disposition in which one projecting section 147 has one insertion section electrode section 32.

For example, three or more insertion section electrode sections 32 may practicably be disposed.

Figure 51:
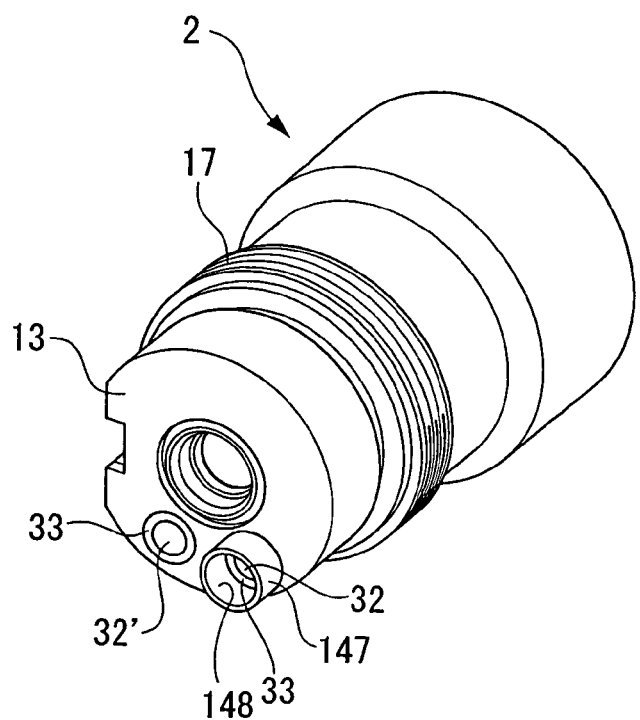
FIG. 51 illustrates modified examples of a projecting section and the insertion section electrode that are shown in FIG. 49.

FIG. 51 furthermore illustrates an example in which a projecting section 147 disposed on the mounting surface 13 has an insertion section electrode section 32 in its hollow section 148, and an insertion section electrode 32' is disposed on a portion of the mounting surface 13 except the hollow section 148.

Figure 52:
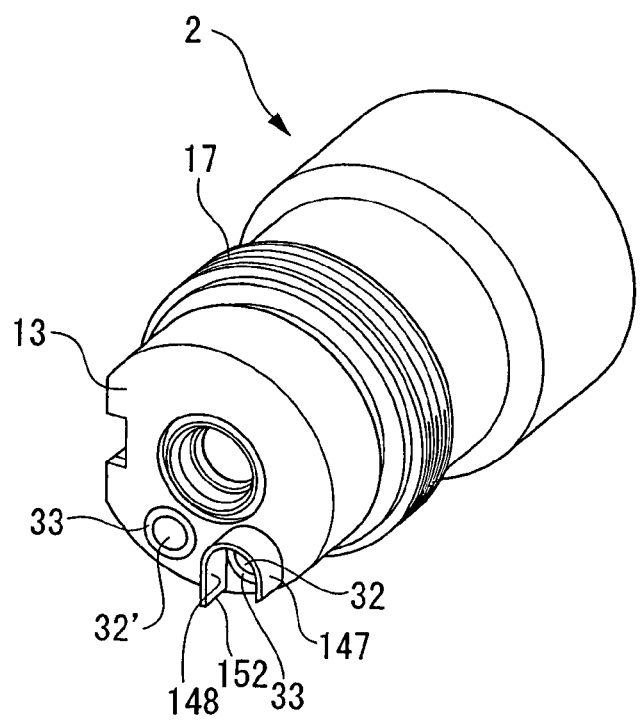
FIG. 52 illustrates modified examples of the recess and the insertion section electrodes that are shown in FIG. 49 and a notch section formed on the recess shown in FIG. 51.

Furthermore, FIG. 52 shows an example in which a projecting section 147 has a notch (notched recess) 152 formed by cutting a portion of the projecting sections 147. If dust has entered the hollow section 148, it would be discharged from the notch section 152 without difficulty. This prevents dust from clogging in the hollow section 148, thereby improving the workability in cleaning inside the recess 148.

Figure 53:
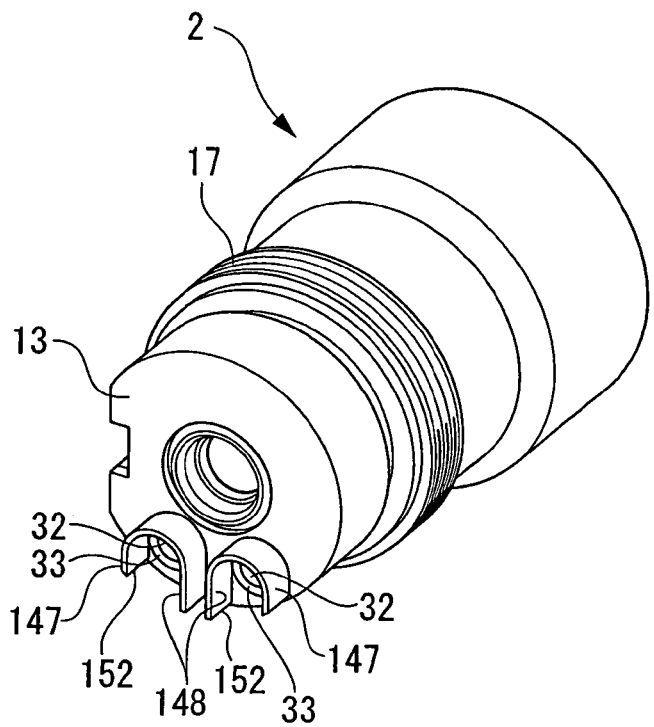
FIG. 53 is a perspective view illustrating modified examples of two projecting sections and the insertion section electrode that are shown in FIG. 49 and a notch section formed on each projecting section.

Also, FIG. 53 practicably shows an example in which two projecting sections 147 each has a notch section 152.

Figure 54:
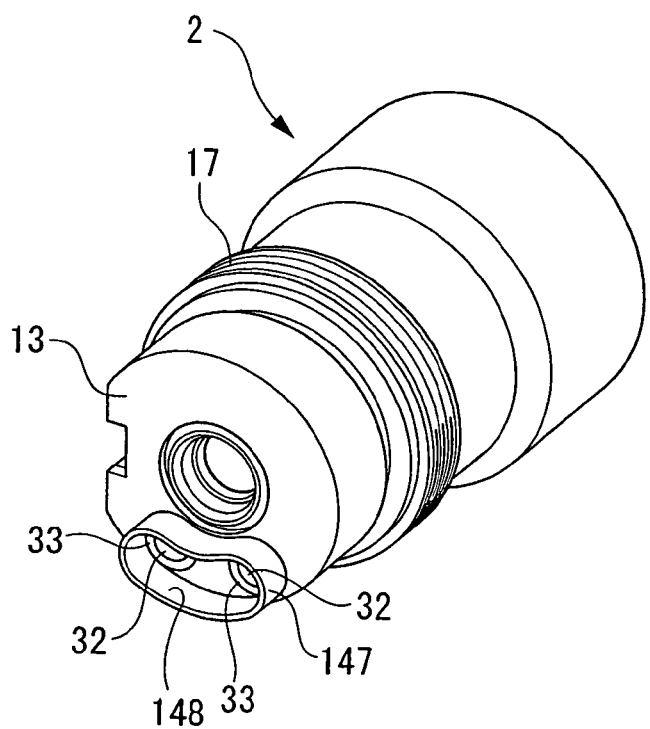
FIG. 54 illustrates modified examples of FIG. 49 having a projecting section having a hollow section accommodating a plurality of the insertion section electrodes.

Furthermore, FIG. 54 practicably shows an example in which two insertion section electrode sections 32 are disposed in a projecting section 147. The simple and low cost configuration that can be shortly obtained facilitates cleaning inside the hollow section 148. The number of insertion section electrode sections 32 disposed in the hollow section 148 in this case may not be limited to two, i.e., it can be arbitrarily modified. That is, a plurality of insertion section electrode sections 32 may be disposed in one common hollow section 148 formed on the mounting surface 13; and some of the insertion section electrode sections 32 may be separately disposed at a plurality of hollow sections 148. Alternatively, some of the insertion section electrode sections 32 may be disposed in the hollow section 148.

Figure 55:
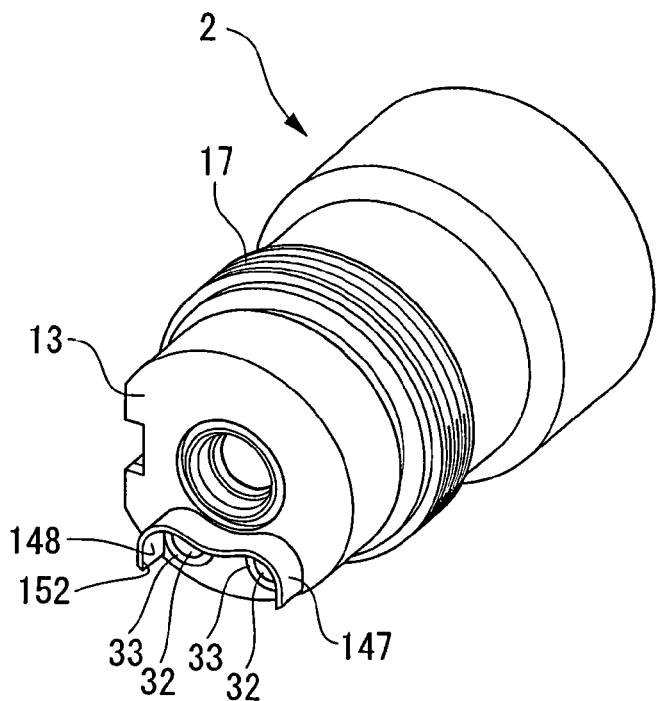
FIG. 55 illustrates modified examples of the projecting section and the insertion section electrodes that are shown in FIG. 49 and a notch section formed on the projecting section shown in FIG. 54.

Also, FIG. 55 practicably shows an example in which a hollow section 148 accommodates a plurality of insertion section electrode sections 32 and has a notch section 152 in the projecting sections 147.

Figure 56:
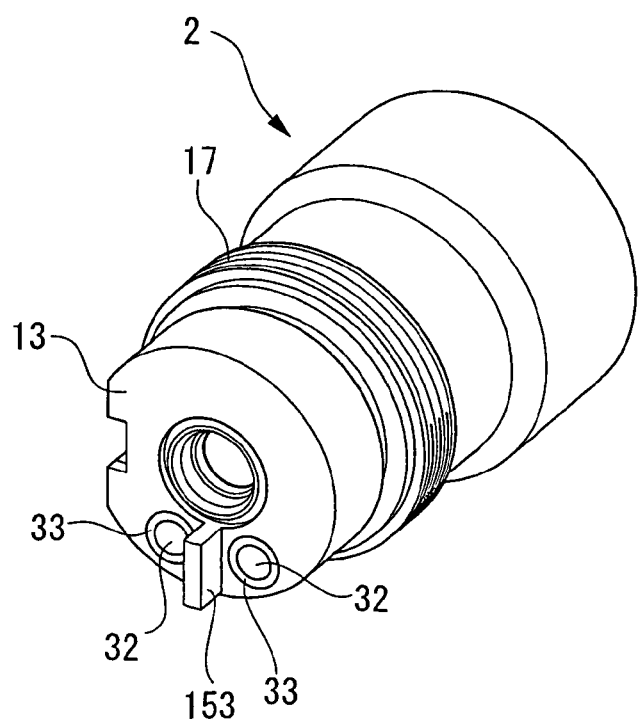
FIG. 56 illustrates modified examples of a projecting section and the insertion section electrodes that are shown in FIG. 49 where a columnar projecting section is provided between the electrodes.

Furthermore, a configuration free of a hollow section 148 may be desirable. To be more specific, projecting sections (projecting sections) 153 projecting in manner of a rectangular parallelepiped shape may be provided between (in the vicinity of) the insertion section electrode sections 32 as shown in FIG. 56. Detaching the optical adapter 12 conceals a part of the insertion section electrode 32 behind the mounting surface 13 because the rectangular parallelepiped protrusion section 153 is disposed in the vicinity of the insertion section electrode sections 32. Accordingly, the simple configuration according to the present embodiment provides an effect similar to that of the previously described fifth embodiment.

In addition, a tapered section (tapered section used for projecting sections) similar to the above configuration and grooves (projecting sections used with a groove), etc., may be provided in the vicinity of the insertion section electrode section 32 in the present embodiment in which the insertion section electrode sections 32 are disposed on the mounting surface 13.

The adapter electrode section 18 according to the above fifth to eighth embodiments is not limited to be connected to the lighting section 11. This may rather be connected to other sensors and electronic components, e.g., adapter recognition sensors and temperature/humidity sensors.

It is in addition understood that the present invention is not limited to the optical adapter 12 of a lateral view type having the lighting section 11 on a side wall section. The lighting section 11 may rather be of a direct view type provided onto the tip of the optical adapter 12.

The insulative member 33 disposed on surfaces of the adapter electrode section 18 and the insertion section electrode section 32 may be anodized instead. Alternatively, the component of the insertion section 2 itself may be of an insulative material, and it may be subjected to an insulation process. This eliminates the necessity of the insulative member 33 covering the adapter electrode section 18 and the insertion section electrode section 32.

The present invention is not limited to the first to fourth embodiments, and various modifications may be made without departing from the spirit of the present invention.

The present invention prevents the generation of an interspace between the inner wall of the opening section and the exterior wall of the electrode terminal with the endoscope adapter attached to the endoscopic insertion section, thereby providing a blockage to the opening section in the attached state of the endoscope adapter without expanding the endoscope adapter and the endoscopic insertion section in size, thus maintaining cleanliness of the electrode terminal in the long term.

Short circuit, failure, and dust entry in the insertion section electrode can be prevented according to the present invention because the insertion section electrode is prevented from projecting from the attaching surface; therefore, the cleanliness of the insertion section electrode can be maintained in the detached state of the adapter from the endoscopic insertion section.

The present invention is effective for use not only in electrical connection to the lighting section but also electrical contacts of sensors and motors, etc. The present invention is also effective for use in electrical contacts of apparatuses subject to electrical connection with respect to optional retrofit requirement.

What is claimed is:

1. An endoscopic apparatus comprising:
   an endoscopic insertion section configured to be inserted into an object to be inspected; and
   an endoscopic adapter configured to be detachably attached to a distal end of the endoscopic insertion section, wherein
   the endoscopic insertion section includes:
      an insertion section attachment surface being disposed to a distal end face of the endoscopic insertion section;
      an insertion section electrode section which is provided in a bottomed cylindrical recess formed on the insertion section attachment surface and is electrically connected to a power supply; and
      an insertion section insulating member which is provided on the insertion section electrode section so as to surround a periphery of the insertion section electrode section; wherein
   the endoscopic adapter includes:
      an attachment hood which detachably connects the endoscopic adapter by fitting the distal end of the endoscopic insertion section;
      an adapter main body which has a first member having an adapter-mounting surface provided in the attachment hood, and a cylindrical-shaped second member which contains the first member therein;
      an adapter electrode section configured to be electrically and directly connected to the insertion section electrode section when the endoscopic adapter is attached to the endoscopic insertion section and has a hollow casing, a coil spring, and an electrode terminal;
      an adapter insulating member being disposed so as to surround a periphery of the adapter electrode section;
      an electrode-mounting hole which is formed on the adapter mounting surface and has a step section on which the adapter insulating member is positioned and fixed,
      the hollow casing is an elongated electro-conductive member having an opening section formed at one end of the longitudinal direction thereof and has a configuration in which a flange section is formed on the opening section to prevent the electrode terminal from detaching, and the coil spring and the electrode terminal are slidably disposed in the hollow casing,
      the coil spring is an electro-conductive member which biases the electrode terminal that is slidably disposed in the hollow casing, the electrode terminal is an elongated electro-conductive member, in which a terminal tip section having an outer diameter that is set to be the same as an inner diameter of the flange section and a terminal base end section which is slidably disposed in the hollow casing and has an outer diameter that is set to be the same as the inner diameter of the hollow casing and larger than the inner diameter of the flange section, are formed in a longitudinal direction, and the electrode terminal biased by the coil spring has a configuration in which the terminal base end section is in contact with the flange section and thus the terminal tip section is capable of projecting from the opening section of the hollow casing.

2. The endoscopic apparatus according to claim 1, wherein the adapter electrode section further includes a sealing member disposed to the one end of the hollow casing and configured to seal a gap between the hollow casing and the electrode terminal.

3. The endoscopic apparatus according to claim 1, wherein the hollow casing is formed by a cylindrical member having a fixed diameter in the longitudinal direction.

4. The endoscopic apparatus according to claim 1, wherein the adapter electrode section further includes a large-diameter portion disposed to a tip of the electrode terminal and having a larger diameter than the electrode terminal.

5. The endoscopic apparatus according to claim 1, wherein the hollow casing has a flange projecting outward in a radial direction thereof from the one end of the hollow casing, and the flange is configured to engage with the adapter insulating member.

6. The endoscopic apparatus according to claim 1, wherein the insertion section hole has an inclined surface gradually increasing in diameter toward the endoscopic adapter, and the inclined surface is connected to the insertion section attachment surface.

7. The endoscopic apparatus according to claim 1, wherein an adapter recess is formed in the adapter attachment surface, and is configured so that the projecting section is inserted therein when the endoscopic adapter is attached to the endoscopic insertion section.

\* \* \* \* \*